United States Patent
Wabl et al.

(10) Patent No.: US 12,096,753 B2
(45) Date of Patent: *Sep. 24, 2024

(54) TRANSGENIC ANIMALS AND METHODS OF USE

(71) Applicant: Trianni, Inc., San Francisco, CA (US)

(72) Inventors: Matthias Wabl, San Francisco, CA (US); Nigel Killeen, Hillborough, CA (US)

( * ) Notice: Subject to any disclaimer, the term of this patent is extended or adjusted under 35 U.S.C. 154(b) by 673 days.

This patent is subject to a terminal disclaimer.

(21) Appl. No.: 17/077,545

(22) Filed: Oct. 22, 2020

(65) Prior Publication Data

US 2021/0037799 A1 Feb. 11, 2021

Related U.S. Application Data

(63) Continuation of application No. 13/818,184, filed as application No. PCT/US2011/045333 on Jul. 26, 2011, now Pat. No. 10,881,084.

(60) Provisional application No. 61/367,809, filed on Jul. 26, 2010.

(51) Int. Cl.
| | |
|---|---|
| *A01K 67/0278* | (2024.01) |
| *A01K 67/027* | (2006.01) |
| *C12N 15/00* | (2006.01) |
| *C12N 15/85* | (2006.01) |
| *C12P 21/00* | (2006.01) |

(52) U.S. Cl.
CPC ........ *A01K 67/0278* (2013.01); *A01K 67/027* (2013.01); *C12N 15/00* (2013.01); *C12N 15/8509* (2013.01); *C12P 21/00* (2013.01); *A01K 2217/07* (2013.01); *A01K 2217/15* (2013.01); *A01K 2227/105* (2013.01); *A01K 2267/01* (2013.01); *C12N 2800/30* (2013.01)

(58) Field of Classification Search
CPC ................................................ A01K 67/0278
See application file for complete search history.

(56) References Cited

U.S. PATENT DOCUMENTS

| | | | |
|---|---|---|---|
| 4,892,824 A | 1/1990 | Skaletsky |
| 5,591,669 A | 1/1997 | Krimpenfort et al. |
| 5,593,598 A | 1/1997 | McGinness et al. |
| 5,612,205 A | 3/1997 | Kay et al. |
| 5,633,425 A | 5/1997 | Lonberg et al. |
| 5,661,016 A | 8/1997 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,985,615 A | 11/1999 | Jakobovits et al. |
| 6,023,010 A | 2/2000 | Krimpenfort et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,162,963 A | 12/2000 | Kucherlapati et al. |
| 6,492,575 B1 | 12/2002 | Wagner et al. |
| 6,570,061 B1 | 5/2003 | Rajewsky et al. |
| 6,586,251 B2 | 7/2003 | Economides |
| 6,596,541 B2 | 7/2003 | Murphy |
| 6,653,113 B1 | 11/2003 | Berns et al. |
| 6,673,986 B1 | 1/2004 | Kucherlapati et al. |
| 6,998,514 B2 | 2/2006 | Bruggeman |
| 7,041,870 B2 | 5/2006 | Kazuma et al. |
| 7,041,871 B1 | 5/2006 | Lonberg |
| 7,064,244 B2 | 6/2006 | Jakobovits et al. |
| 7,105,348 B2 | 9/2006 | Murphy |
| 7,129,084 B2 | 10/2006 | Buelow |
| 7,145,056 B2 | 12/2006 | Jakobovits et al. |
| 7,205,148 B2 | 4/2007 | Economides et al. |
| 7,294,754 B2 | 11/2007 | Poueymirou et al. |
| 7,473,557 B2 | 1/2009 | Economides et al. |
| 7,476,536 B2 | 1/2009 | Kuroiwa et al. |
| 7,501,552 B2 | 3/2009 | Lonberg |
| 7,541,513 B2 | 6/2009 | Bruggeman |
| 7,659,442 B2 | 2/2010 | Poueymirou et al. |
| 7,868,223 B2 | 1/2011 | Tomizuka et al. |
| 8,158,419 B2 | 4/2012 | Lonberg |
| 8,232,449 B2 | 7/2012 | Tanamachi |

(Continued)

FOREIGN PATENT DOCUMENTS

| | | |
|---|---|---|
| CA | 2089661 C | 3/1992 |
| EP | 0817835 A1 | 1/1998 |

(Continued)

OTHER PUBLICATIONS

Lonberg N. (2005, Nature Biotechnology, vol. 23(9), pp. 1117-1125) (Year: 2005).*
Third-Party Submission dated Mar. 31, 2021 in U.S. Appl. No. 16/849,847, filed Apr. 15, 2020.
Communication mailed Apr. 2, 2021 regarding Third Party Submission.
Office Action issued Aug. 22, 2019 in U.S. Appl. No. 15/603,334.
Amendment/Reply under 37 C.F.R § 1.111 filed Sep. 19, 2019 in response to the Non-Final Office Action issued Aug. 22, 2019 in U.S. Appl. No. 15/603,334.
Amendment/Reply under 37 C.F.R § 1.114 filled Jul. 10, 2017 in response to the Final Office Action issued Feb. 24, 2017 in U.S. Appl. No. 13/818,184.
Bao, Yonghua et al., "Molecular characterization of the VH repertoire in Canis familiaris," Veterinary Immunology and Immunopathology, 2010, vol. 137, pp. 64-75.

(Continued)

*Primary Examiner* — Anoop K Singh
*Assistant Examiner* — David A Montanari
(74) *Attorney, Agent, or Firm* — MEDLER FERRO WOODHOUSE & MILLS PLLC

(57) ABSTRACT

The present invention comprises non-human vertebrate cells and non-human mammals having a genome comprising an introduced partially human immunoglobulin region, said introduced region comprising human $V_H$ coding sequences and non-coding $V_H$ sequences based on the endogenous genome of the non-human mammal.

11 Claims, 11 Drawing Sheets

(56) References Cited

U.S. PATENT DOCUMENTS

| | | | |
|---|---|---|---|
| 8,293,480 | B2 | 10/2012 | Lonberg |
| 8,367,888 | B2 | 2/2013 | Bruggeman |
| 8,502,018 | B2 | 8/2013 | Murphy |
| 8,754,287 | B2 | 6/2014 | MacDonald et al. |
| 9,012,717 | B2 | 4/2015 | MacDonald et al. |
| 9,580,491 | B2 | 2/2017 | Green et al. |
| 10,494,445 | B2 | 12/2019 | Green et al. |
| 10,526,420 | B2 | 1/2020 | Green et al. |
| 10,575,504 | B2 | 3/2020 | Green et al. |
| 10,604,587 | B2 | 3/2020 | Green et al. |
| 10,618,977 | B2 | 4/2020 | Green et al. |
| 10,626,188 | B2 | 4/2020 | Green et al. |
| 10,662,255 | B2 | 5/2020 | Green et al. |
| 2003/0017534 | A1 | 1/2003 | Buelow |
| 2006/0015957 | A1 | 1/2006 | Lonberg |
| 2007/0061900 | A1 | 3/2007 | Murphy |
| 2009/0055943 | A1 | 2/2009 | Economides |
| 2009/0111126 | A1 | 4/2009 | Akamatsu |
| 2009/0136950 | A1 | 5/2009 | Dubridge |
| 2010/0317539 | A1 | 12/2010 | Yu |
| 2011/0145937 | A1 | 6/2011 | MacDonald et al. |
| 2011/0236378 | A1 | 9/2011 | Green |
| 2011/0258710 | A1 | 10/2011 | Murphy |
| 2011/0283376 | A1 | 11/2011 | Murphy |
| 2012/0047585 | A1 | 2/2012 | Rohrer et al. |
| 2012/0073004 | A1 | 3/2012 | MacDonald |
| 2012/0090041 | A1 | 4/2012 | Buelow |
| 2012/0096572 | A1 | 4/2012 | MacDonald et al. |
| 2013/0137101 | A1 | 5/2013 | Economides |
| 2013/0263292 | A1 | 10/2013 | Liang |
| 2013/0333057 | A1 | 12/2013 | MacDonald et al. |
| 2014/0283153 | A1 | 9/2014 | Trianni |
| 2015/0183820 | A1 | 7/2015 | Honda et al. |
| 2017/0058052 | A1 | 3/2017 | Wabl et al. |
| 2017/0188557 | A1 | 7/2017 | Green et al. |
| 2017/0218090 | A1 | 8/2017 | Green et al. |
| 2017/0226162 | A1 | 8/2017 | Killeen et al. |
| 2017/0303517 | A1 | 10/2017 | Wabl |
| 2017/0306352 | A1 | 10/2017 | Wabl |
| 2018/0230238 | A1 | 8/2018 | Wabl et al. |
| 2020/0181285 | A1 | 6/2020 | Green et al. |
| 2020/0181286 | A1 | 6/2020 | Green et al. |
| 2020/0407464 | A1 | 12/2020 | Green et al. |

FOREIGN PATENT DOCUMENTS

| | | | |
|---|---|---|---|
| EP | 1399559 | A2 | 3/2004 |
| EP | 1399575 | A2 | 3/2004 |
| EP | 2264163 | A2 | 12/2010 |
| EP | 2517556 | A2 | 10/2012 |
| EP | 2517557 | A2 | 10/2012 |
| GB | 2398784 | A | 9/2004 |
| GB | 2561352 | A | 10/2018 |
| WO | 90/04036 | A1 | 4/1990 |
| WO | 90/10077 | A1 | 9/1990 |
| WO | 92/03918 | A1 | 3/1992 |
| WO | 94/25585 | A1 | 11/1994 |
| WO | 96/40915 | A2 | 12/1996 |
| WO | 99/45962 | A1 | 6/1999 |
| WO | 01/09187 | A2 | 2/2001 |
| WO | 02/12437 | A2 | 2/2002 |
| WO | 02/066618 | A1 | 8/2002 |
| WO | 02/066630 | A1 | 8/2002 |
| WO | 2008/070367 | A2 | 6/2008 |
| WO | 2008/081197 | A1 | 7/2008 |
| WO | 2008/151081 | A1 | 12/2008 |
| WO | 2009/013620 | A2 | 1/2009 |
| WO | 2009/157771 | A2 | 12/2009 |
| WO | 2010/039900 | A2 | 4/2010 |
| WO | 2011/004192 | A1 | 1/2011 |
| WO | 2011/123708 | A2 | 10/2011 |
| WO | 2011/158009 | A1 | 12/2011 |
| WO | 2011/163311 | A1 | 12/2011 |
| WO | 2012/018610 | A2 | 2/2012 |
| WO | 2012/123949 | A1 | 9/2012 |
| WO | 2013/022782 | A1 | 2/2013 |
| WO | 2013/092720 | A1 | 6/2013 |
| WO | 2013/096142 | A1 | 6/2013 |
| WO | 2013/138681 | A1 | 9/2013 |
| WO | 2013/171505 | A2 | 11/2013 |
| WO | 2014/013075 | A2 | 1/2014 |
| WO | 2015/112790 | A2 | 7/2015 |
| WO | 2015/188141 | A2 | 12/2015 |
| WO | 2017/035252 | A1 | 3/2017 |
| WO | 2017/095939 | A1 | 6/2017 |
| WO | 2018/128691 | A1 | 7/2018 |
| WO | 2018/189520 | A1 | 10/2018 |
| WO | 2019/113065 | A1 | 6/2019 |

OTHER PUBLICATIONS

Guss, Bengt et al., "Structure of the IgG-binding regions of streptococcal protein G," The EMBO Journal, 1986, vol. 5, No. 7, pp. 1567-1575.

Melidoni, Anna N. et al., "Selecting antagonistic antibodies that control differentiation through inducible expression in embryonic stem cells," PNAS, Oct. 29, 2013, vol. 110, No. 44, pp. 17802-17807.

Proudhon, Charlotte et al., "Long Range Regulation of V(D)J Recombination", Adv Immunol., 2015, vol. 128, pp. 123-182.

Ramsden, Dale A. et al., "Conservation of sequence in recombination signal sequence spacers", Nucleic Acids Research, 1994, vol. 22, No. 10, pp. 1785-1796.

Tunyaplin, Chalnarong et al., "Characterization of the B lymphocyte-induced maturation protein-1 (Blimp-1) gene, mRNA isoforms and basal promoter," Nucleic Acids Research, 2000, vol. 28, No. 24, pp. 4846-4855.

Any references not provided herewith were previously cited and submitted in U.S. Appl. No. 13/818,184, filed May 6, 2013 to which this application claims priority.

Altschul et al., "Basic local alignment search tool," J Mol Biol 215:403-410 (1990).

Avitahl et al., "A 125 bp region of the Ig $V_H1$ promoter is sufficient to confer lymphocyte-specific expression in transgenic mice," Int Immunol 8(9):1359-1366 (1996).

Bao et al., "Molecular characterization of the VH repertoire in *Canis familiaris*," Vet Immunol Immunopathol 137:64-75 (2010).

Barthold, "Genetically altered mice: phenotypes, no phenotypes, and Faux phenotypes," Genetica 122: 75-88 (2004).

Bentley et al., "Unrearranged immunoglobulin variable region genes have a functional promoter," Nucleic Acids Res 10:1841-1856 (1982).

Berman et al., "Content and organization of the human Ig $_H$ locus: definition of three new $V_H$ families and linkage to the Ig $C_H$ locus," EMBO J 7(3):727-738 (1988).

Blankenstein et al., "Immunoglobulin $V_H$ region genes of the mouse are organized in overlapping cluster," Eur J Immunol 17:1351-1357 (1987).

Brekke et al., "Assembly and analysis of the mouse immunoglobulin kappa gene sequence," Immunogenetics 56:490-505 (2004).

Brevini et al., "No shortcuts to pig embryonic stem cells," Theriogenology 74: 544-550 (2010).

Bruggemann, "The Preparation of Human Antibodies from Mice Harbouring Human Immunoglobulin Loci," Transgenic Animals: Generation and Use, pp. 397-402, Ed. L.M. Houdebine, CRC Press (1997).

Buta et al., "Reconsidering pluripotency tests: Do we sill need teratoma assays?" Stem Cell Research 11: 552-562 (2013).

Casellas et al., "Igκ allelic inclusion is a consequence of receptor editing," J Exp Med 204(1):153-160 (2007).

Cesari et al, "Elk-1 knock-out mice engineered by Flp recombinase-mediated cassette exchange," Genesis 38:87-92 (2004).

Choe et al., "Fc-Binding Ligands of Immunoglobulin G: An Overview of High Affinity Proteins and Peptides," Materials 9: 994 (2016).

Church et al., "Lineage-specific biology revealed by a finished genome assembly of the mouse," PLoS Biol 7:e1000112 (2009).

(56) References Cited

OTHER PUBLICATIONS

Clargo et al., "The rapid generation of recombinant functional monoclonal antibodies from individual, antigen-specific bone marrow-derived plasma cells isolated using a novel fluorescence-based method," *mAbs* 6(1): 143-159 (2013).
Clarke et al., "An immunoglobulin promoter region is unaltered by DNA rearrangement and somatic mutation during B-cell development," *Nucleic Acids Res* 10:7731-7749 (1982).
De Bono, Bernard et al., "$V_H$ Gene Segments in the Mouse and Human Genomes", J. Mol. Biol., 2004, vol. 342, pp. 131-143.
Decaire et al., "A Publicly Available PCR Methods Laboratory Manual and Supporting Material," *J Microbiol Biol Educ* 16:269-270 (2015).
Downing et al., "Technical assessment of the first 20 years of research using mouse embryonic stem cell lines," *Stem Cells* 22:1168-1180 (2004).
Doyen et al., "Analysis of promoter and enhancer cell type specificities and the regulation of immunoglobulin gene expression," *Gene* 50:321-331 (1986).
Featherstone et al., "The Mouse Immunoglobulin Heavy Chain V-D Intergenic Sequence Contains Insulators That May Regulate Ordered V(D)J Recombination," *J Biol Chem* 285:9327-9338 (2010).
Fishwild et al., "High-avidity human IgG kappa monoclonal antibodies from a novel strain of minilocus transgenic mice," *Nat Biotechnol*, 14:845-851 (1996).
Garcia-Arocena, "Same Mutation, Different Phenotype?" The Jackson Laboratory, Blog Post dated Nov. 11, 2014. Accessed at https://www.jax.org/news-and-insights/jax-blog/2014/november/same-mutation-different-phenotype.
Gellert, "Molecular analysis of V(D)J recombination," *Annu Rev Genet* 26:425-446 (1992).
Gomez et al., "Derivation of cat embryonic stem-like cells from in vitro-produced blastocytes on homologous and heterologous feeder cells," *Theriogenology* 74: 498-515 (2010).
Gopal et al., "Contribution of promoter to tissue-specific expression of the mouse immunoglobulin kappa gene," *Science* 229:1102-1104 (1985).
Gunasekaran et al., "Enhancing Antibody Fc Heterodimer Formation through Electrostatic Steering Effects," *J Biol Chem* 285:19637-19646 (2010).
Hauser, Jannek et al., "Allelic Exclusion of IgH through Inhibition of E2A in a VDJ Recombination Complex", The Journal of Immunology, vol. 192, 2014, pp. 2460-2470.
Heiman-Patterson et al., "Effect of genetic background on phenotype variability in transgenic mouse models of amyotrophic lateral sclerosis: A window of opportunity in the search for genetic modifiers," *Amyotrophic Laterla Sclerosis* 00: 1-8 (2011).
Hengartner et al., "Assignment of genes for immunoglobulin kappa and heavy chains to chromosomes 6 and 12 in mouse," *Proc Natl Acad Sci USA* 75:4494-4498 (1978).
Hong et al., "Derivation and Characterization of Embryonic Stem Cell Lines Derived from Transgenic Fischer 344 and Dark Agouti Rats," *Stem Cells and Development* 21(9): 1571-1586 (2012).
Honjo et al., ed. *Immunoglobulin Genes*. San Diego, CA: Academic Press Inc., 1989; Chapters 4-6 and 17.
Ichihara et al., "Organization of human immunoglobulin heavy chain diversity gene loci," *EMBO J* 7(13):4141-4150 (1988).
International Human Genome Sequencing Consortium, "Finishing the euchromatic sequence of the human genome," *Nature* 431:931-945 (2004).
Ivics et al., "Germline transgenesis in rodents by pronuclear microinjection of Sleeping Beauty transposons," *Nature Protocols* 9(4); 773-793 (2014).
Johnston et al., "Complete Sequence Assembly and Characterization of the C57BL/6 Mouse Ig Heavy Chain V Region," *J Immunol* 176:4221-4234 (2006).
Jones et al., "Replacing the complementarity-determining regions in a human antibody with those from a amouse," *Nature* 321:522-525 (1986).

Jung et al., "Unraveling V(D)J Recombination: Insights into Gene Regulation," *Cell* 116:299-311 (2004).
Kabat et al., "Variable region genes for the immunoglobulin framework are assembled from small segments of DNA—A hypothesis," *Proc Natl Acad Sci USA* 75:2429-2433 (1978).
Kabat et al., "Evidence supporting somatic assembly of the DNA segments (minigenes), coding for the framework, and complementarity-determining segments of immunoglobulin variable regions," *J Exp Med* 149:1299-1313 (1979).
Kawasaki et al., "One-Megabase Sequence Analysis of the Human Immunoglobulin λ Gene Locus," *Genome Res* 7:250-261 (1997).
Kitamura et al., "Targeted disruption of μ chain membrane exon causes loss of heavy-chain allelic exclusion," *Nature* 356:154-156 (1992).
Kontermann et al., "Bispecific antibodies," *Drug Discov Today* 20(7):838-847 (2015).
Kozak, "An analysis of 5'-noncoding sequences from 699 vertebrate messenger RNAs," *Nucleic Acids Res* 15:8125-8148 (1987).
Kurosawa et al., "Organization, Structure, and Assembly of Immunoglobulin Heavy Chain Diversity DNA Segments," *J Exp Med* 155:201-218 (1982).
Lander et al., "Initial sequencing and analysis of the human genome," *Nature* 2001, 409:860-921 (2001).
Landsteiner et al., "On the Specificity of Serological Reactions with Simple Chemical Compounds (Inhibition Reactions)," *J Exp Med* 54:295-305 (1931).
Lee et al., "Genome data mining for everyone," *BMB Reports* 41(11):757-764 (2008).
Lefranc et al., "IMGT unique numbering for immunoglobulin and T cell receptor variable domains and Ig superfamily V-like domains," *Dev Comp Immunol* 27:55-77 (2003).
Li et al., "Biochemical Analysis of the Regulatory T Cell Protein Lymphocyte Activation Gene-3 (LAG-3; CD223)," *Journal of Immunology* 173: 6806-6812 (2004).
Liu et al., "A Novel Antibody Engineering Strategy for Making Monovalent Bispecific Heterodimeric IgG Antibodies by Electrostatic Steering Mechanism," *J Biol Chem* 290:7535-7362 (2015).
Lutz et al., "Pro-B cells sense productive immunoglobulin heavy chain rearrangement irrespective of polypeptide production," *Proc Nat Acad Sci USA* 108(26):10644-10649 (2011).
Ma et al., "DNA Synthesis, Assembly and Applications in Synthetic Biology," *Curr Opin Chem Biol* 16:260-267 (2012).
Manz et al., "Analysis and sorting of live cells according to secreted molecules relocated to a cell-surface affinity matrix," *Proceedings of the National Academy of Science USA* 92: 1921-1925 (1995).
Mason et al., "Transcription cell type specificity is conferred by an immunoglobulin VH gene promoter that includes a functional consensus sequence," *Cell* 41:479-487 (1985).
Matsuda et al., "The Complete Nucleotide Sequence of the Human Immunoglobulin Heavy Chain Variable Region Locus," *J Exp Med* 188(11):2151-2162 (1998).
McLenachan et al., "Flow-cytometric analysis of mouse embryonic stem cell lipofection using small and large DNA constructs," *Genomics* 89:708-720 (2007).
Meng et al., "Optimized production of transgenic buffalo embryos and offspring by cytoplasmic zygote injection," *Journal of Animal Science and Biotechnology* 6: 44 (2015).
Misra et al., "Gene targeting in the mouse: advances in introduction of transgenes into the genome by homologous recombination," *Endocrine* 19:229-238 (2002).
Munoz et al., "Conventional pluripotency markers are unspecific for bovine embryonic-derived cell-lines," *Theriogenology* 69: 1159-1164 (2008).
Mouse Genome Sequencing Consortium, "Initial sequencing and comparative analysis of the mouse genome," *Nature* 420:520-562 (2002).
Paris et al., "Equine embryos and embryonic stem cells: Defining reliable markers of pluripotency," *Theriogenology* 74: 516-524 (2010).
Pinder et al., "Isolation and Characterization of Antigen-Specific Plasmablasts Using a Novel Flow Cytometry-Based Ig Capture Assay," *Journal of Immunology* 199(12): 4180-4188 (2017).

(56) References Cited

OTHER PUBLICATIONS

Priat et al., "A whole-genome radiation hybrid map of the dog genome," *Genomics* 54(3):361-378 (1998).
Price et al., "Engineered cell surface expression of membrane immunoglobulin as a means to identify monoclonal antibody-secreting hybridomas," *Journal of Immunological Methods* 343:28-41 (2009).
Rajewsky et al., "Allelic exclusion model questioned," Scientific Correspondence, *Nature* 359:371-372 (1992).
Ristevski, "Making better transgenic models: conditional, temporal, and spatial approaches," *Mol Biotechnol* 29:153-163 (2005).
Roebroek et al., "Mutant Lrp1 knock-in mice generated by recombinase-mediated cassette exchange reveal differential importance of the NPXY motifs in the intracellular domain of LRP1 for normal fetal development," *Mol Cell Biol* 26:605-616 (2006).
Saiki et al., "Analysis of enzymatically amplified beta-globin and HLA-DQ alpha DNA with allele-specific oligonucleotide probes," *Nature* 324:163-166 (1986).
Sakano et al., "Identification and nucleotide sequence of a diversity DNA segment (D) of immunoglobulin heavy-chain genes," *Nature* 290:562-565 (1981).
Schellenberg et al., "Pre-mRNA splicing: a complex picture in higher definition," *Trends Biochem Sci* 33:243-246 (2008).
Sharon, "The invariant tryptophan in an H chain V region is not essential to antibody binding," *J Immunol* 140:2666-2669 (1988).
Sonoda et al, "B Cell Development under the Condition of Allelic Inclusion," *Immunity* 6:225-233 (1997).
Tonegawa, "Somatic generation of antibody diversity," *Nature* 302:575-581 (1983).
Tong et al., "Production of p53 gene knockout rats by homologous recombination in embryonic stem cells," *Nature* 467: 211-215 (2010).
Toor et al., "Structural insights into RNA splicing," *Curr Opin Struct Biol* 19:260-266 (2009).
Venter et al., "The sequence of the human genome," *Science* 291:1304-1351 (2001).
Vetterman et al., "Allelic exclusion of immunoglobulin genes: models and mechanisms," *Immunol Rev* 237:22-42 (2010).

Van Keuren et al., "Generating Transgenic Mice from Bacterial Artificial Chromosomes: Transgenesis Efficiency, Integration and Expression Outcomes," *Transgenic Research* 18(5): 769-785 (2009).
Verkoczy, Laurent et al., "Human Ig knockin mice to study the development and regulation of HIV-1 broadly neutralizing antibodies", *Immunological Reviews*, 2017, vol. 275, pp. 89-107.
Von Heijne, "Protein targeting signals," *Curr Opin Cell Biol* 2:604-608 (1990).
Wabl et al., "Allelic exclusion model questioned," Scientific Correspondence, *Nature* 359:370-371 (1992).
Wallace, Helen A.C. et al., "Manipulating the Mouse Genome to Engineer Precise Functional Syntenic Replacements with Human Sequence", Cell, Jan. 12, 2007, vol. 128, pp. 197-209.
Waisman, Ari et al., IgG1 B cell receptor signaling is inhibited by CD22 and promotes the development of B cells whose survival is less dependent on Igα/β.
Wang, Feng et al., "Reshaping Antibody Diversity", Cell, Jun. 6, 2013, vol. 153, No. 6, pp. 1379-1393.
West et al., "Genome Editing in Large Animals," *Journal of Equine Veterinary Science* 41: 1-6 (2014).
Xiong et al., "Chemical gene synthesis: strategies, softwares, error corrections, and applications," *FEMS Microbiol Rev* 32:522-540 (2008).
Zhang, Shaosen et al., "A New and Robust Method of Tethering IgG Surrogate Antigens on Lipid Bilayer Membranes to Facilitate the TIRFM Based Live Cell and Single Molecule Imaging Experiments", PloS ONE, May 2013, vol. 8, No. 5, pp. 1-14.
Zhou, Hongzhe et al., "Generation of Monoclonal Antibodies against Highly Conserved Antigens", PloS ONE, Jun. 2009, vol. 4, No. 6, pp. 1-6.
Final Office Action in co-pending U.S. Appl. No. 13/818,184, dated Jun. 1, 2018.
Non-Final Office Action issued in U.S. Appl. No. 13/818,184, dated Mar. 8, 2019.
Non-final Office Action issued in U.S. Appl. No. 15/603,347, dated Jun. 28, 2019.
U.S. Appl. No. 61/319,690, filed Mar. 31, 2010 in the name of Ablexis, LLC.
U.S. Appl. No. 61/361,302, filed Jul. 2, 2010 in the name of Ablexis, LLC.

* cited by examiner

TRANSGENIC ANIMALS AND METHODS OF USE

CROSS-REFERENCE TO RELATED APPLICATIONS

This application is a continuation application of U.S. application Ser. No. 13/818,184, which is a National Stage Entry of PCT/US2011/045333, filed Jul. 26, 2011, which claims the benefit of U.S. Provisional Patent Application No. 61/367,809, filed Jul. 26, 2010, the disclosures of which are incorporated herein by reference.

FIELD OF THE INVENTION

This invention related to transgenic vertebrates, and more specifically to transgenic vertebrates for the development of human therapeutics.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The genes encoding human and mouse immunoglobulins have been extensively characterized. As of 1988, it was known that H chain variable regions are encoded by three separate germline gene segments, variable ($V_H$), diversity (D), and joining (J) segments and L chain variable regions are encoded by $V_L$ and $J_L$ segments. See, Berman et al. (1988) EMBO J. 7:727-738. Berman et al. also indicate that human $V_H$ gene segments can be identified based on homology with murine or previously isolated human $V_H$ genes and provide a detailed analysis of the content and organization of the human Ig $V_H$ locus including an alignment of nucleotide sequences of several $V_H$ human genes (using the Beckman MicroGenie sequence analysis program) and describe the conserved heptamer and nonamer recombination sequences, the leader intron and the regulatory octamer sequence located upstream of the $V_H$ leader sequence. Sakano et al. (1981) Nature 290:562-565 describe the nucleotide sequence and structure of a diversity (D) segment of the immunoglobulin heavy chain genes including recombination signal sequences (RSSs) flanking the D gene segments having 12 base pair (bp) long spacer sequences and explain that D gene segments recombine with the 23 bp RSS of $V_H$ and $J_H$ gene segments in accordance with the 12/23 bp rule. Blankenstein and Kruwinkel (1987) Eur. J. Immunol. 17:1351-1357 provide a low resolution physical map of the mouse variable heavy chain region. The generation of transgenic animals, such as mice having varied immunoglobulin loci, has allowed the use of such transgenic animals in various research and development applications, e.g., in drug discovery and basic research into various biological systems. The generation of transgenic mice hearing human immunoglobulin genes is described in International Application WO 90/10077 and WO 90/04036. WO 90/04036 describes a transgenic mouse with an integrated human immunoglobulin "mini" locus. WO 90/10077 describes a vector containing the immunoglobulin dominant control region for use in generating transgenic animals.

Numerous methods have been developed for replacing endogenous mouse immunoglobulin regions with human immunoglobulin sequences to create partially- or fully-human antibodies for drug discovery purposes. Examples of such mice include those described in, for example, U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669. Many of the fully humanized immunoglobulin mice have antibody production below normal rates due to less efficient V(D)J recombination, and limited antibody production caused from partial gene complement. Others in which the mouse coding sequence have been "swapped" with human sequences are very time consuming and expensive to create due to the approach of replacing individual mouse exons with the syntenic human counterpart.

Based on the foregoing, it is clear that a need exists for efficient and cost-effective methods of efficiently producing human antibodies. More particularly, there is a need in the art for non-human vertebrates comprising human immunoglobulin regions and transgenic animals having the ability to properly respond to an antigen.

In accordance with the foregoing object transgenic non-human animals are provided which are capable of producing an antibody with human V regions.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention comprises non-human vertebrate cells and non-human vertebrates having a genome comprising an introduced partially human immunoglobulin region, said introduced region comprising human immunoglobulin variable region locus coding sequences and non-coding sequences based on the endogenous immunoglobulin variable region locus of the non-human vertebrate. Preferably, the transgenic cells and animals of the invention have genomes in which part or all of the endogenous immunoglobulin region is removed.

At a minimum, the production of human monoclonal antibodies in non-human vertebrates requires that the host have at least one locus that will express human heavy chain immunoglobulin proteins and one locus that will express human light chain immunoglobulin proteins.

In some aspects, the partially human immunoglobulin variable region locus comprises human $V_H$ coding sequences and non-coding $V_H$ sequences based on the endogenous $V_H$ region of the non-human vertebrate. In these aspects, the partially human immunoglobulin variable region locus further comprises human D and J gene coding sequences and non-coding D and J gene sequences based on the endogenous genome of the non-human vertebrate host.

In other aspects, the immunoglobulin region comprises an introduced region comprising human $V_L$ coding sequences and non-coding $V_L$ sequences based on the endogenous $V_L$ region of the non-human vertebrate. More preferably, the introduced partially human immunoglobulin region comprising human $V_L$ coding sequences further comprises human J gene coding sequences and non-coding J gene sequences based on the endogenous genome of the non-human vertebrate host.

In certain aspects, the vertebrate is a mammal, and preferably the mammal is a rodent, e.g., a mouse or rat. In other aspects, the vertebrate is avian, e.g., a chicken.

In one specific aspect, the invention provides a method for generating a non-human vertebrate cell comprising a partially human immunoglobulin region, said method comprising: a) introducing two or more recombinase targeting sites into a non-human vertebrate cell and integrating at least one site in the cell's genome upstream and at least one site downstream of a genomic region comprising an endogenous immunoglobulin variable region locus; and b) introducing a partially human immunoglobulin variable region locus comprising human immunoglobulin variable region coding sequences and non-coding sequences based on the endogenous immunoglobulin variable region of the non-human vertebrate host into the non-human vertebrate host cell via recombinase mediated exchange.

In a specific aspect of this method, the introduced partially human immunoglobulin region comprises human $V_H$ gene coding regions, and further comprises i) human D and J gene coding sequences and ii) non-coding D and J gene and pre-DJ sequences based on the endogenous genome of the non-human vertebrate host. The partially human immunoglobulin regions are preferably introduced into the host cell using recombinase targeting sites that are introduced upstream of the endogenous $V_H$ immunoglobulin genes and downstream of the endogenous D and J gene region.

In other aspects, the $V_H$ gene coding regions derive (at least partially) from other sources—e.g., they could be rationally or otherwise designed sequences, sequences that are a combination of human and other designed sequences, or sequences from other species, such as nonhuman primates.

In yet another specific aspect, the introduced partially human immunoglobulin region comprises human $V_L$ gene coding regions, and further comprises i) human J gene coding sequences and ii) non-coding J gene sequences based on the endogenous genome of the non-human vertebrate host. The partially human immunoglobulin regions are preferably introduced into the host cell using recombinase targeting sites that are introduced upstream of the endogenous $V_L$ immunoglobulin genes and downstream of the endogenous J region.

Preferably, the partially human immunoglobulin region is synthesized as a single nucleic acid, and introduced into the non-human vertebrate host cell as a single nucleic acid region. The partially human immunoglobulin region may also be synthesized in two or more contiguous segments, and introduced to the vertebrate host cell in these discrete segments. The partially human nucleic acid can also be produced using recombinant methods and isolated prior to introduction of the nucleic acid to the non-human vertebrate host cell.

In another preferred aspect, the method further provides deleting the genomic region flanked by the two introduced recombinase sites prior to step b).

In another aspect, the invention provides methods for generating a non-human vertebrate cell comprising a partially human immunoglobulin region, said method comprising: a) introducing two or more site-specific recombination sites that are not capable of recombining with one another into the genome of a cell of a non-human vertebrate host, wherein at least one recombination site is introduced upstream of an endogenous immunoglobulin variable region locus and at least one recombination site is introduced downstream of the endogenous immunoglobulin variable region locus; b) providing a vector comprising a partially human immunoglobulin region having i) human immunoglobulin variable region coding sequences and ii) non-coding sequences based on an endogenous immunoglobulin variable region to the host cell, wherein the partially human region is flanked by the same two site-specific recombination sites that flank the endogenous variable immunoglobulin region of the host cell of a); c) introducing the vector of step b) and a site specific recombinase capable of recognizing the two recombinase sites to the cell; d) allowing a recombination event to occur between the genome of the cell of a) and the partially human immunoglobulin region, resulting in a replacement of the endogenous immunoglobulin variable region locus with the partially human immunoglobulin region locus. In a specific aspect of this method, the partially human immunoglobulin region comprises $V_H$ immunoglobulin gene coding sequences, and further comprises i) human D and J gene coding sequences and ii) non-coding D and J gene and pre-DJ sequences based on the endogenous genome of the non-human vertebrate host. The recombinase targeting sites are introduced upstream of the endogenous $V_H$ immunoglobulin genes and downstream of the endogenous D and J gene sequences.

In another specific aspect of this method, the method further provides deleting the genomic region flanked by the two introduced recombinase sites prior to step c).

The invention provides yet another method for generating a transgenic non-human vertebrate cell, said method comprising: a) providing a non-human vertebrate cell having a genome that comprises two sets of site-specific recombination sites that are not capable of recombining with one another, and which flank a portion of an endogenous immunoglobulin region of the host genome; b) deleting the portion of the endogenous immunoglobulin variable region locus of the genome by introduction of a recombinase that recognizes a first set of site-specific recombination sites, wherein such deletion in the genome retains the second set of site-specific recombination sites; c) providing a vector comprising a partially human immunoglobulin variable region locus comprising human coding sequences and non-coding sequences based on an endogenous immunoglobulin variable region flanked by the second set of site-specific recombination sites; d) introducing the vector of step c) and a site specific recombinase capable of recognizing the second set of recombinase sites to the cell; and e) allowing a recombination event to occur between the genome of the cell and the partially human immunoglobulin variable region locus, resulting in a replacement of the endogenous immunoglobulin variable region locus with the partially human immunoglobulin variable region locus.

Preferably, the non-human mammalian cell for use in each of the above methods is a mammalian cell, and more preferably a mammalian embryonic stem (ES) cell. In other aspects, the cell may be an avian cell, and preferably an avian primordial germ cell.

Once the cells have been subjected to the replacement of the endogenous immunoglobulin variable region locus, cells comprising the introduced partially human immunoglobulin variable region are selected and preferably isolated. In a preferred aspect of the invention, the cells are non-human mammalian embryonic stem (ES) cells, and the isolated ES cell is then utilized to create a transgenic non-human mammal expressing the partially human immunoglobulin variable region locus. In other aspects, the cells are primordial germ cells, and the isolated germ cell is then utilized to create a transgenic non-human bird expressing the partially human immunoglobulin variable region.

In a specific aspect, the invention provides a method for generating a non-human mammalian cell comprising a partially human immunoglobulin region, said method comprising: a) providing an non-human mammalian embryonic stem (ES) cell having a genome that contains two site-specific recombination sites that are not capable of recombining with each other, and which flank a portion of the immunoglobulin region; b) providing a vector comprising a partially human immunoglobulin region comprising human immunoglobulin variable region coding sequences and non-coding sequences based on an endogenous immunoglobulin variable region, said partially human region flanked by the same two site-specific recombination sites that flank the portion of the immunoglobulin region in the ES cell; c) bringing the ES cell and said vector into contact with a site specific recombinase capable of recognizing the two recombinase sites under appropriate conditions to promote a recombination event resulting in the replacement of the endogenous portion of immunoglobulin region with the partially human immunoglobulin region in the ES cell.

In another aspect, the invention provides a method for generating a transgenic non-human mammal comprising a partially human immunoglobulin region, said method comprising: a) introducing one or more site-specific recombination sites that are not capable of recombining with one another into the genome of a cell of a non-human vertebrate host; b) providing a vector comprising a partially human immunoglobulin region having i) human variable coding sequences and ii) non-coding sequences based on the endogenous variable region, wherein the partially human region is flanked by the same site-specific recombination sites as those introduced to the genome of the host cell of a); c) introducing the vector of step b) and a site specific recombinase capable of recognizing one set of recombinase sites to the cell; d) allowing a recombination event to occur between the genome of the cell of a) and the partially human immunoglobulin region, resulting in a replacement of the endogenous immunoglobulin variable region with the partially human immunoglobulin region; e) selecting a cell which comprises the partially human immunoglobulin region; and f) utilizing the cell to create a transgenic animal comprising the partially human immunoglobulin region.

In a specific aspect, the partially human immunoglobulin region comprises human $V_H$ coding regions, human D and J gene coding sequences, and non-coding D and J gene and pre-DJ sequences based on the endogenous genome of the non-human vertebrate host. The site-specific recombination sites are then introduced upstream of an endogenous $V_H$ immunoglobulin genes and downstream of the endogenous D and J gene regions.

The invention provides another method for generating a transgenic non-human animal comprising a partially human immunoglobulin region, said method comprising: a) providing a non-human vertebrate cell having a genome that comprises two sets of site-specific recombination sites that are not capable of recombining with one another, and which flank a portion of an endogenous immunoglobulin variable region locus of the host genome; b) deleting the portion of the endogenous immunoglobulin region of the host genome by introduction of a recombinase that recognizes a first set of site-specific recombination sites, wherein such deletion in the genome retains the second set of site-specific recombination sites; c) providing a vector comprising a partially human immunoglobulin variable region locus having human coding sequences and non-coding sequences based on an endogenous immunoglobulin variable region locus flanked by the second set of site-specific recombination sites; d) introducing the vector of step c) and a site specific recombinase capable of recognizing the second set of site-specific recombination sites to the cell; e) allowing a recombination event to occur between the genome of the cell and the partially human immunoglobulin variable region, resulting in a replacement of the endogenous immunoglobulin region with the partially human immunoglobulin variable region; f) selecting a cell which comprises the partially human immunoglobulin variable region; and g) utilizing the cell to create a transgenic animal comprising the partially human immunoglobulin variable region.

The invention provides yet another method for generating a transgenic non-human mammal comprising a partially human immunoglobulin region, said method comprising: a) providing an non-human mammalian embryonic stem (ES) cell having a genome that contains two site-specific recombination sites that are not capable of recombining with each other, and which flank a portion of the immunoglobulin region; b) providing a vector comprising a partially human immunoglobulin region comprising human variable coding sequences and non-coding sequences based on the endogenous variable gene region, said partially human region flanked by the same two site-specific recombination sites that flank the portion of the immunoglobulin region in the ES cell; c) bringing said ES cell and said vector into contact with a site specific recombinase capable of recognizing the two recombinase sites under appropriate conditions to promote a recombination event resulting in the replacement of the endogenous portion of immunoglobulin region with the partially human immunoglobulin region in the ES cell; d) selecting an ES cell which comprises the replaced portion of nucleic acid and using said embryonic stem cell; and e) utilizing the cell to create a transgenic animal comprising the partially human immunoglobulin variable region locus to generate a heterozygous partially human animal.

In a specific aspect of the invention, the transgenic non-human vertebrates are mammals, and preferably the mammals are rodents, e.g., a mouse or a rat. In other aspects, the transgenic non-human vertebrates are avian, e.g., a chicken.

It is an object of the invention to provide non-human vertebrate cells and non-human transgenic mammals expressing an introduced immunoglobulin variable region locus having human variable region coding sequences and non-coding sequences based on the endogenous host genome.

Further, it is an object to provide B-cells from transgenic animals which are capable of expressing partially human antibodies having human $V_H$ sequences, where such B-cells are immortalized to provide a source of a monoclonal antibody specific for a particular antigen.

It is yet another object to provide human variable regions cloned from B cells for use in the production and/or optimization of antibodies for diagnostic and therapeutic uses.

It is a further object of the invention to provide hybridoma cells that are capable of producing partially human monoclonal antibodies having human variable region sequences.

These and other aspects, objects and features are described in more detail below.

DEFINITIONS

Figure 1:
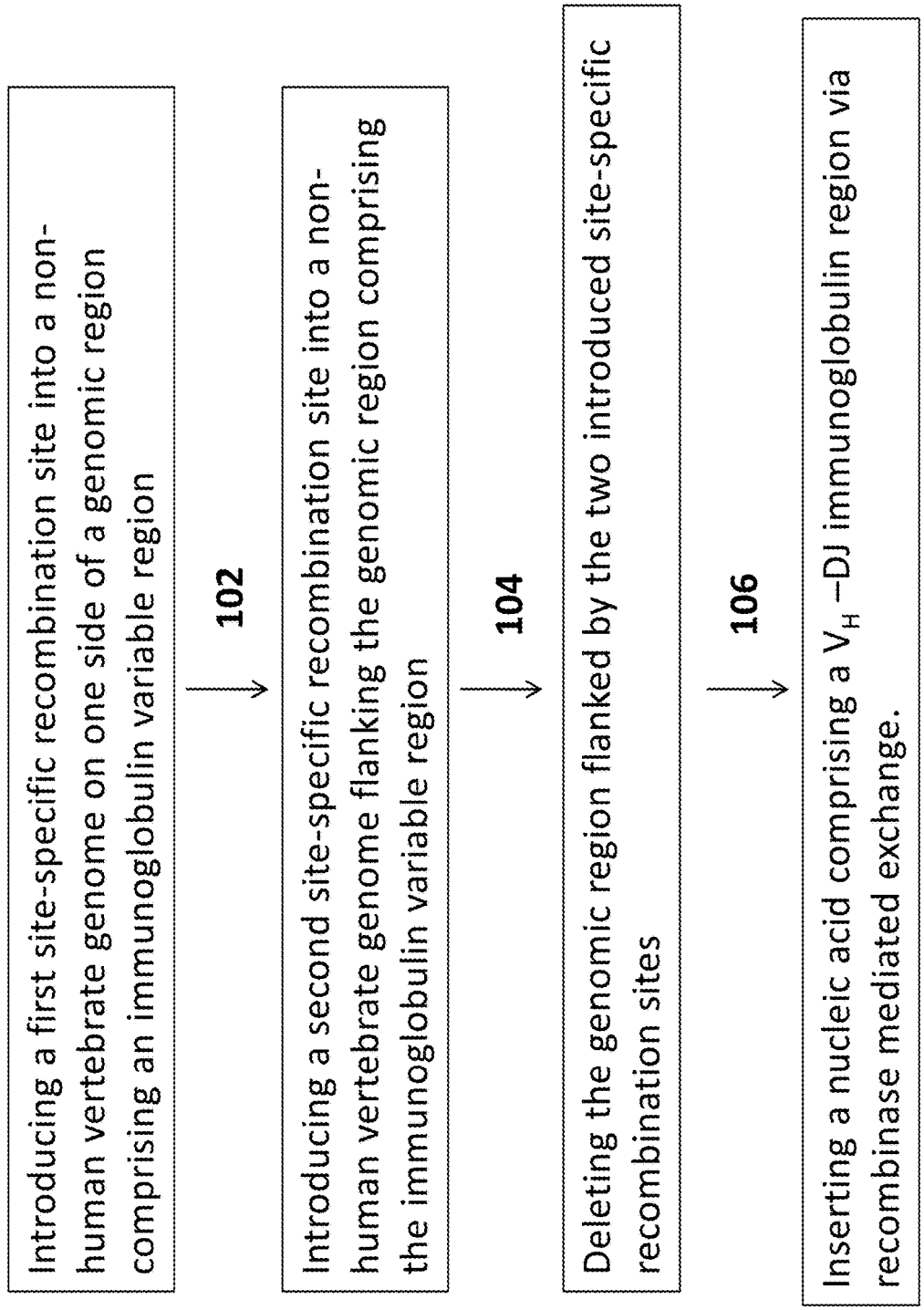
FIG. 1 illustrates a flow chart setting forth one exemplary method from the preferred embodiment of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"partially human" as used herein refers to a nucleic acid having sequences from both a human and a non-human mammal or an animal comprising a nucleic acid having sequences from both a human and a non-human mammal. In the context of partially human sequences of the invention, the partially human nucleic acids have sequences of human immunoglobulin coding regions and sequences based on the non-coding sequences of the endogenous immunoglobulin region of the non-human mammal. The term "based on" when used with reference to endogenous non-coding sequences from a non-human mammal refers to sequences that correspond to the non-coding sequence and share a relatively high degree of homology with the non-coding sequences of the endogenous loci of the host mammal, e.g., the mammal from which the ES cell is derived. Preferably, the non-coding sequences share at least an 80%, more preferably 90% homology with the corresponding non-coding sequences found in the endogenous loci of the non-human vertebrate host cell into which a partially human molecule comprising the non-coding sequences is being introduced.

The term "homology targeting vector" refers to a vector comprising a nucleic acid encoding a targeting sequence, a site-specific recombination site, and optionally a selectable marker gene, which is used to modify immunoglobulin region using homology-mediated recombination in a host cell. For example, a homology targeting vector can be used in the present invention to introduce a site-specific recombination site into particular region of a host cell genome.

The term "immunoglobulin variable region" as used herein refers to a nucleotide sequence that encodes all or a portion of a variable region of an antibody molecule or all or a portion of a regulatory nucleotide sequence that controls expression of an antibody molecule. Immunoglobulin regions for heavy chains may include but are not limited to all or a portion of the V, D, J, and switch regions, including introns. Immunoglobulin region for light chains may include but are not limited to the V and J regions, their upstream flanking sequences, introns, associated with or adjacent to the light chain constant region gene.

"Site-specific recombination" refers to a process of recombination between two compatible recombination sites including any of the following three events: a) deletion of a preselected nucleic acid flanked by the recombination sites; b) inversion of the nucleotide sequence of a preselected nucleic acid flanked by recombination sites, and c) reciprocal exchange of nucleic acid regions proximate to recombination sites located on different nucleic acid molecules. It is to be understood that this reciprocal exchange of nucleic acid segments results in an integration event if one or both of the nucleic acid molecules are circular.

The term "targeting sequence" refers to a sequence homologous to DNA sequences in the genome of a cell that flank or occur adjacent to the region of an immunoglobulin region to be modified. The flanking or adjacent sequence may be within the locus itself or upstream or downstream of coding sequences in the genome of the host cell. Targeting sequences are inserted into recombinant DNA vectors which are used to transfect such that sequences to be inserted into the cell genome, such as the sequence of a recombination site, are flanked by the targeting sequences of the vector.

The term "site-specific targeting vector" as used herein refers to a vector comprising a nucleic acid encoding a site-specific recombination site, a partially human nucleic acid, and optionally a selectable marker gene, which is used to modify an endogenous immunoglobulin region in a host using recombinase-mediated site-specific recombination. The recombination site of the targeting vector is suitable for site-specific recombination with another corresponding recombination site which has been inserted into a genomic sequence of the host cell (e.g., via a homology targeting vector), adjacent to an immunoglobulin region which is to be modified. Integration of a partially human sequence into a recombination site in an immunoglobulin region results in replacement of the endogenous region by the introduced partially human region.

The term "transgene" is used herein to describe genetic material which has been or is about to be artificially inserted into the genome of a cell, and particularly a cell of a vertebrate host animal. The term "transgene" as used herein refers to a partially human nucleic acid, e.g., a partially human nucleic acid in the form of an expression construct and/or a targeting vector.

By "transgenic animal" is meant a non-human animal, usually a mammal, having an exogenous nucleic acid sequence present as an extrachromosomal element in a portion of its cells or stably integrated into its germ line DNA (i.e., in the genomic sequence of most or all of its cells). In the present invention, a partially human nucleic acid is introduced into the germ line of such transgenic animals by genetic manipulation of, for example, embryos or embryonic stem cells of the host animal according to methods well known in the art.

A "vector" includes plasmids and viruses and any DNA or RNA molecule, whether self-replicating or not, which can be used to transform or transfect a cell.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry, $5^{th}$* Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a locus" refers to one or more loci, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

In the humoral immune system, a diverse antibody repertoire is produced by combinatorial and junctional diversity of IgH (Igh) and IgL chain (Igl) gene loci in a process termed V(D)J recombination. In the developing B cell, the first recombination event to occur is between one D and one J gene segment of the heavy chain locus, and the DNA between these two genes is deleted. This D-J recombination is followed by the joining of one V gene from a region upstream of the newly formed DJ complex, forming a rearranged V(D)J gene. All other genes between V and D segments of the new V(D)J gene are now deleted from the individual B cell's genome. This rearranged gene is ultimately expressed on the B cell surface as an IgH polypeptide, which associates with an IgL to form the B cell receptor. The murine and human Ig loci are highly complex, spanning regions of approximately 2 Mb, containing several constant region gene segments, J gene segments, D gene segments and larger number of variable genes.

The present invention provides non-human vertebrate cells comprising an introduced partially human nucleic acid comprising coding regions for human variable regions and non-coding sequences from the vertebrate host genome, e.g., mouse genomic non-coding sequences when the host mammal is a mouse. This partially human nucleic acid allows the transgenic animal to produce a heavy chain repertoire comprising human $V_H$ regions, while retaining the regulatory sequences and other elements that can be found within the intervening sequences in a particular host genome that help to promote efficient antibody production and antigenic recognition. The present invention comprises the use of a synthetic or recombinantly produced partially human region comprising both human coding sequences and non-human non-coding sequences from a $V_H$ locus.

Because the methods of the invention can take advantage of two or more sets of site-specific recombination sites within the engineered genome, the recombination step allows multiple insertions to be made into the partially human locus.

In preferred aspects of the invention, this partially human region to be introduced into a host vertebrate cell comprises all or a substantial number of the known human $V_H$ genes. In some instances, however, it may be desirable to use a subset of such $V_H$ genes, and in specific instances even as few as one human $V_H$ coding sequences may be used in the cells and the animals of the invention.

The preferred aspects of the invention comprise non-human mammals and mammalian cells comprising a partially human immunoglobulin locus that comprises human $V_H$ genes and further comprises D and J gene human coding regions and pre-DJ sequences based on the endogenous genome of the non-human mammalian host. In certain aspects, the introduced partially human region can comprise one or more fully recombined V(D)J segments.

In a specific aspect of the invention, the transgenic non-human mammal comprises an introduced nucleic acid comprising multiple human $V_H$ genes with intervening sequences based on the intervening sequences in the non-human mammalian host loci and human coding regions for human D and J genes. In a particularly preferred aspect, the partially human nucleic acid comprises the human $V_H$ genes, a pre-D region based on the genome of the non-human mammalian host, e.g., the mouse genome, and a human D and J exons.

In an exemplary embodiment, as set forth in more detail in the Examples section, the entire endogenous $V_H$ immunoglobulin locus of the mouse (including the J558 locus) is deleted, and the $V_H$ exons of the J558 $V_H$ region locus of a mouse are replaced with a nucleic acid comprising 44 of the human $V_H$ genes, which, as a result, are interspersed with non-coding regions that correspond to the non-coding sequences of mouse. The complete introduced immunoglobulin $V_H$ region further comprises human D and J exons as well as $V_H$ genes. In this aspect, the 10 Kb pre-D region comprises mouse sequences, while the D and J regions comprise human coding sequences. Preferably, the D and J regions are provided as a human DJ coding region comprising human D genes and human J genes.

The methods of the invention utilize a combination of homologous recombination and site-specific recombination to create the cells and animals of the invention. A homology targeting vector is first used to introduce the site-specific recombination sites into the host mammal genome at the desired location in the endogenous immunoglobulin loci. Insertion of a site-specific recombination site into a genomic sequence via homologous recombination of an associated targeting sequence with genomic DNA in vivo preferably does not modify an amino acid sequence of the antibody molecule which is expressed by the transfected cell. This approach maintains the proper transcription and translation of the immunoglobulin genes which produce the desired antibody after insertion of recombination sites and, optionally, any additional sequence such as a selectable marker gene. However, in some cases it is possible to insert a recombinase site and other sequences into an immunoglobulin locus sequence such that an amino acid sequence of the antibody molecule is altered by the insertion, but the antibody still retains sufficient functionality for the desired purpose, and the invention envisions encompassing such insertions as well.

Exemplary methodologies for homologous recombination are described in U.S. Pat. Nos. 6,689,610; 6,204,061; 5,631,153; 5,627,059; 5,487,992; and 5,464,764, each of which is incorporated by reference in its entirety.

In specific aspects of the invention, the homology targeting vector can be utilized to replace certain sequences within the endogenous genome as well as introducing the site-specific recombination sites and selectable markers. For example, the homology targeting used to introduce elements 3' of the $V_H$ gene region may be used to replace the mouse pre-D and DJ sequences with the human equivalents.

Site-Specific Recombination

Site-specific recombination differs from general homologous recombination in that short specific DNA sequences, which are required for the recombinase recognition, are the only sites at which recombination occurs. Site-specific recombination requires specialized recombinases to recognize the sites and catalyze the recombination at these sites. A number of bacteriophage and yeast derived site-specific recombination systems, each comprising a recombinase and specific cognate sites, have been shown to work in eukaryotic cells for the purpose of DNA integration and are therefore applicable for use in the present invention, and these include the bacteriophage P1 Cre/lox, yeast FLP-FRT system, and the Dre system of the tyrosine family of site-specific recombinases. Such systems and methods of use are described, for example, in U.S. Pat. Nos. 7,422,889; 7,112,715; 6,956,146; 6,774,279; 5,677,177; 5,885,836; 5,654,182; and 4,959,317, which are incorporated herein by reference to teach methods of using such recombinases. The recombinase mediated cassette exchange (RMCE) procedure is facilitated by usage of the combination of wild-type and mutant loxP (or FRT etc) sites together with negative selection. It will occur, however, when only non-mutant sites are used and/or in the absence of selection. But the efficiency is very low because excision rather than insertion reactions are favored and (without incorporating positive selection) there will be no enrichment for appropriately mutated cells.

Other systems of the tyrosine family such as bacteriophage lambda Int integrase, HK2022 integrase, and in addition systems belonging to the separate serine family of recombinases such as bacteriophage phiC31, R4Tp901 integrases are known to work in mammalian cells using their respective recombination sites (Tronche, F. et al. 2002), and are also applicable for use in the present invention.

The methods of the invention preferably utilize site-specific recombination sites that utilize the same recombinase, but which do not facilitate recombination between the sites. For example, a Lox P site and a mutated Lox P site can be integrated into the genome of a host, but introduction of Cre into the host will not cause the two sites to facilitate recombination; rather, the LoxP site will recombine with another LoxP site, and the mutated site will only recombine with another likewise mutated LoxP site. Examples of such mutated recombination sites include those that contain a combination of inverted repeats or those which comprise recombination sites having mutant spacer sequences. For example, two classes of variant recombinase sites are available to engineer stable Cre-loxP integrative recombination. Both exploit sequence mutations in the Cre recognition sequence, either within the 8 bp spacer region or the 13-bp inverted repeats. Spacer mutants such as lox511 (Hoess R H et al., *Nucleic Acids Res* 1986, 14:2287-2300), lox5171 and lox2272 (Lee G and Saito I, *Gene* 1998, 216:55-65), m2, m3, m7, and m11 (Langer S J et al., *Nucleic Acids Res* 2002, 30:3067-3077) recombine readily with themselves but have a markedly reduced rate of recombination with the wild-type site. This class of mutants has been exploited for DNA insertion by recombinase mediated cassette exchange (RMCE) using non-interacting Cre-Lox recombination sites and non-interacting FLP recombination sites (Baer A and Bode J, *Curr Opin Biotechnol* 2001, 12:473-480; Albert H et al., *Plant J* 1995, 7:649-659; Seibler J and Bode J, *Biochemistry* 1997, 36:1740-1747; Schlake T and Bode J, *Biochemistry* 1994, 33:12746-12751).

Inverted repeat mutants represent the second class of variant recombinase sites. For example, LoxP sites can contain altered bases in the left inverted repeat (LE mutant) or the right inverted repeat (RE mutant). An LE mutant, lox71, has 5 bp on the 5' end of the left inverted repeat that is changed from the wild type sequence to TACCG (Araki K et al, *Nucleic Acids Res* 1997, 25:868-872). Similarly, the RE mutant, lox66, has the five 3'-most bases changed to CGGTA. Inverted repeat mutants are used for integrating plasmid inserts into chromosomal DNA with the LE mutant designated as the "target" chromosomal loxP site into which the "donor" RE mutant recombines. Post-recombination, loxP sites are located in cis, flanking the inserted segment. The mechanism of recombination is such that post-recombination one loxP site is a double mutant (containing both the LE and RE inverted repeat mutations) and the other is wild type (Lee L and Sadowski P D, *Prog Nucleic Acid Res Mol Biol* 2005, 80:1-42; Lee L and Sadowski P D, *J Mol Biol* 2003, 326:397-412). The double mutant is sufficiently different from the wild-type site that it is unrecognized by Cre recombinase and the inserted segment is not excised.

In certain aspects, site-specific recombination sites can be introduced into introns, as opposed to coding nucleic acid regions or regulatory sequences. This may avoid inadvertently disrupting any regulatory sequences or coding regions necessary for proper antibody expression upon insertion of site-specific recombination sites into the genome of the animal cell.

Introduction of the site-specific recombination sites may be achieved by conventional homologous recombination techniques. Such techniques are described in references such as e.g., Sambrook and Russell (2001) (Molecular cloning: a laboratory manual 3rd edn (Cold Spring Harbor, N.Y.: Cold Spring Harbor Laboratory Press) and Nagy, A. (2003). (Manipulating the mouse embryo: a laboratory manual, 3rd edn (Cold Spring Harbor, N.Y.: Cold Spring Harbor Laboratory Press). Genetic Recombination: Nucleic acid, Homology (biology), Homologous recombination, Non-homologous end joining, DNA repair, Bacteria, Eukaryote, Meiosis, Adaptive immune system, V(D)J recombination by Frederic P. Miller, Agnes F. Vandome, and John McBrewster (Paperback-Dec. 23, 2009).

Specific recombination into the genome can be facilitated using vectors designed for positive or negative selection as known in the art. In order to facilitate identification of cells that have undergone the replacement reaction, an appropriate genetic marker system may be employed and cells selected by, for example use of a selection medium. However, in order to ensure that the genome sequence is substantially free of extraneous nucleic acid sequences at or adjacent to the two end points of the replacement interval, desirably the marker system/gene can be removed following selection of the cells containing the replaced nucleic acid.

In one preferred aspect of the methods of the present invention, cells in which the replacement of all or part of the endogenous immunoglobulin has taken place are negatively selected upon exposure to a toxin or drug. For example, cells that retain expression of HSV-TK can be selected through use of appropriate use of nucleoside analogues such as gancyclovir. In another aspect of the invention, cells comprising the deletion of the endogenous immunoglobulin region may be positively selected by use of a marker gene, which can optionally be removed from the cells following or as a result of the recombination event. A positive selection system that may be used is based on the use of two non-functional portions of a marker gene, such as HPRT, that are brought together through the recombination event. These two portions are brought into functional association upon a successful replacement reaction being carried out and wherein the functionally reconstituted marker gene is flanked on either side by further site-specific recombination sites (which are different to the site-specific recombination sites used for the replacement reaction), such that the marker gene can be excised from the genome, using an appropriate site-specific recombinase.

The recombinase may be provided as a purified protein, or a construct transiently expressed within the cell in order to provide the recombinase activity. Alternatively, the cell may be used to generate a transgenic animal, which may be crossed with an animal which expresses said recombinase, in order to produce progeny which lack the marker gene and associated recombination sites.

Generation of Transgenic Animals

In specific aspects, the invention provides methods for the creation of transgenic animals comprising the introduced partially human immunoglobulin region.

In one aspect, the host cell utilized for replacement of the endogenous immunoglobulin genes is an embryonic stem (ES) cell, which can then be utilized to create a transgenic mammal. Thus, in accordance with one aspect, the methods of the invention further comprise: isolating an embryonic stem cell which comprises the introduced partially human immunoglobulin region and using said ES cell to generate a transgenic animal that contains the replaced partially immunoglobulin locus.

In another example, the transgenic animal is avian, and the animal is produced using primordial germ cells. Thus, in accordance with another aspect, the methods of the invention further comprise: isolating a primordial germ cell which comprises the introduced partially human immunoglobulin region and using said germ cell to generate a transgenic animal that contains the replaced partially immunoglobulin locus. Methods for production of such transgenic avians are disclosed, e.g., in U.S. Pat. Nos. 7,323,618 and 7,145,057, which are incorporated herein by reference.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to terms and numbers used (e.g., vectors, amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

The examples illustrate targeting by both a 5' vector and a 3' vector that flank a site of recombination and introduction of synthetic DNA. It will be apparent to one skilled in art upon reading the specification that the 5' vector targeting can take place first followed by the 3', or the 3' vector targeting can take place followed by the 5' vector. In some circumstances, targeting can be carried out simultaneously with dual detection mechanisms.

Example 1: Introduction of a Partially Human Immunoglobulin Region into the $V_H$ Gene Locus of a Mouse Genome An exemplary method for replacing a portion of a mammalian genome with partially human immunoglobulin region is illustrated in FIGS. 1-6. FIG. 1 shows a flow chart illustrating the different steps of this exemplary aspect of the methods of the invention. This method provides introducing a first site-specific recombination site into the mammalian genome, which may be introduced either 5' or 3' of an endogenous $V_H$ region of the mammalian genome. This is then followed by the introduction 102 of a second site-specific recombination site into the mammalian genome, which in combination with the first site-specific recombination site flanks the endogenous immunoglobulin region. The flanked endogenous region is deleted 104 and a synthetic nucleic acid comprising both human and non-human sequences is introduced 106 via recombinase mediated exchange.

Figure 2:
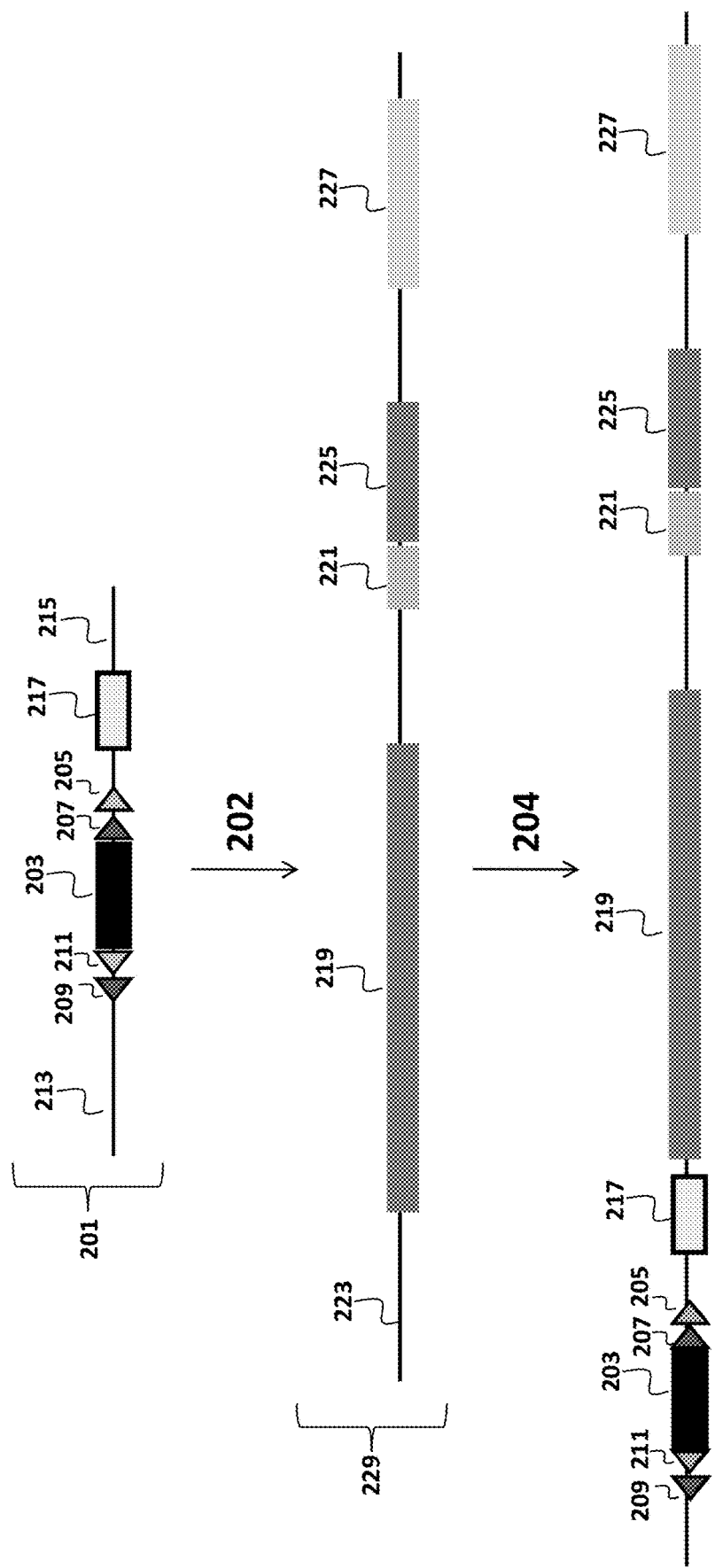
FIG. 2 is a schematic diagram illustrating the introduction of a first set of site-specific recombination sites into the genome of a non-human mammalian cell via a homology targeting vector.

An exemplary method illustrating the introduction of a partially human mouse-human immunoglobulin region into the genomic locus of a mouse ES cell is illustrated in more detail in FIGS. 2-6. In FIG. 2, a homology targeting vector 201 is provided comprising a puromycin phosphotransferase-thymidine kinase fusion protein (puroΔTK) 203 flanked by two different recombinase recognition sites, e.g., FRT 207 and loxP 205, for Flp and Cre, and modified sites e.g., for FRT 209 and loxP 211, which have the inability to recombine with the unmodified sites 207 and 205, respectively. The targeting vector comprises a human diphtheria toxin receptor (hDTR) cDNA 217 for use in negative selection of cells expressing the introduced construct in future steps. The targeting vector also optionally comprises a visual marker such as a fluorescent green protein (GFP) (not shown). The regions 213 and 215 are homologous to the 5' and 3' portions, respectively, of a contiguous region 223 in the endogenous mouse locus that is 5' of the genomic region 219 comprising the mouse endogenous $V_H$ genes. The homology targeting vector 201 is introduced 202 to the mouse ES cell, which has an immunoglobulin region 229 comprising endogenous $V_H$ genes 219, the pre-D region 221, the J gene region 225 and the constant gene region 227 of the immunoglobulin region. The site specific recombination sites and the hDTR cDNA 217 of the homology targeting vector 201 is integrated 204 into the mouse genome 5' of the mouse endogenous $V_H$ gene region.

Figure 3:
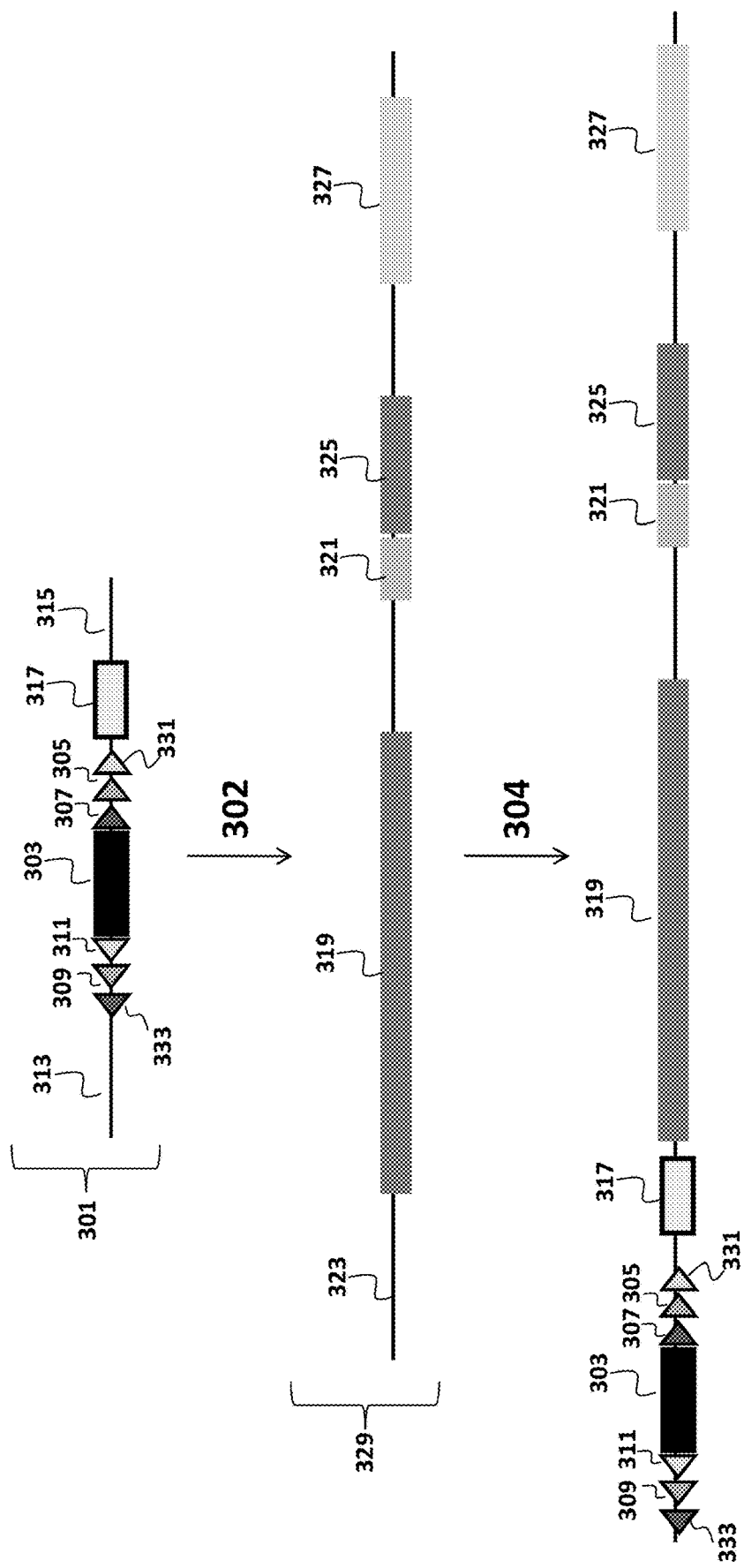
FIG. 3 is another schematic diagram illustrating the introduction of a first set of site-specific recombination sites into the genome of a non-human mammalian cell via a homology targeting vector.

FIG. 3 illustrates effectively the same approach as FIG. 2, except that an additional set of site-specific recombination sites is added, e.g., a Rox site 331 and a modified Rox site 333 for use with the Dre recombinase. In FIG. 3 a homology targeting vector 301 is provided comprising a puromycin phosphotransferase-thymidine kinase fusion protein 303 flanked by recombinase recognition sites FRT 307, loxP 305, and Rox 331 and modified sites for FRT 309 loxP 311 and Rox 333, which have the inability to recombine with the unmodified sites 307, 305 and 331, respectively. The targeting vector also comprises a human diphtheria toxin receptor (hDTR) cDNA 317. The regions 313 and 315 are homologous to the 5' and 3' portions, respectively, of a contiguous region 323 in the endogenous mouse locus that is 5' of the genomic region 319 comprising the mouse endogenous $V_H$ genes. The homology targeting vector 301 is introduced 302 to the mouse immunoglobulin region 329, which comprises the endogenous $V_H$ genes 319, the pre-D region 321, the J gene region 325 and the constant gene region 327 of the immunoglobulin region. The site specific recombination sites and the hDTR cDNA 317 of the homology targeting vector 301 is integrated 304 into the mouse genome 5' of the mouse endogenous $V_H$ gene region.

Figure 4:
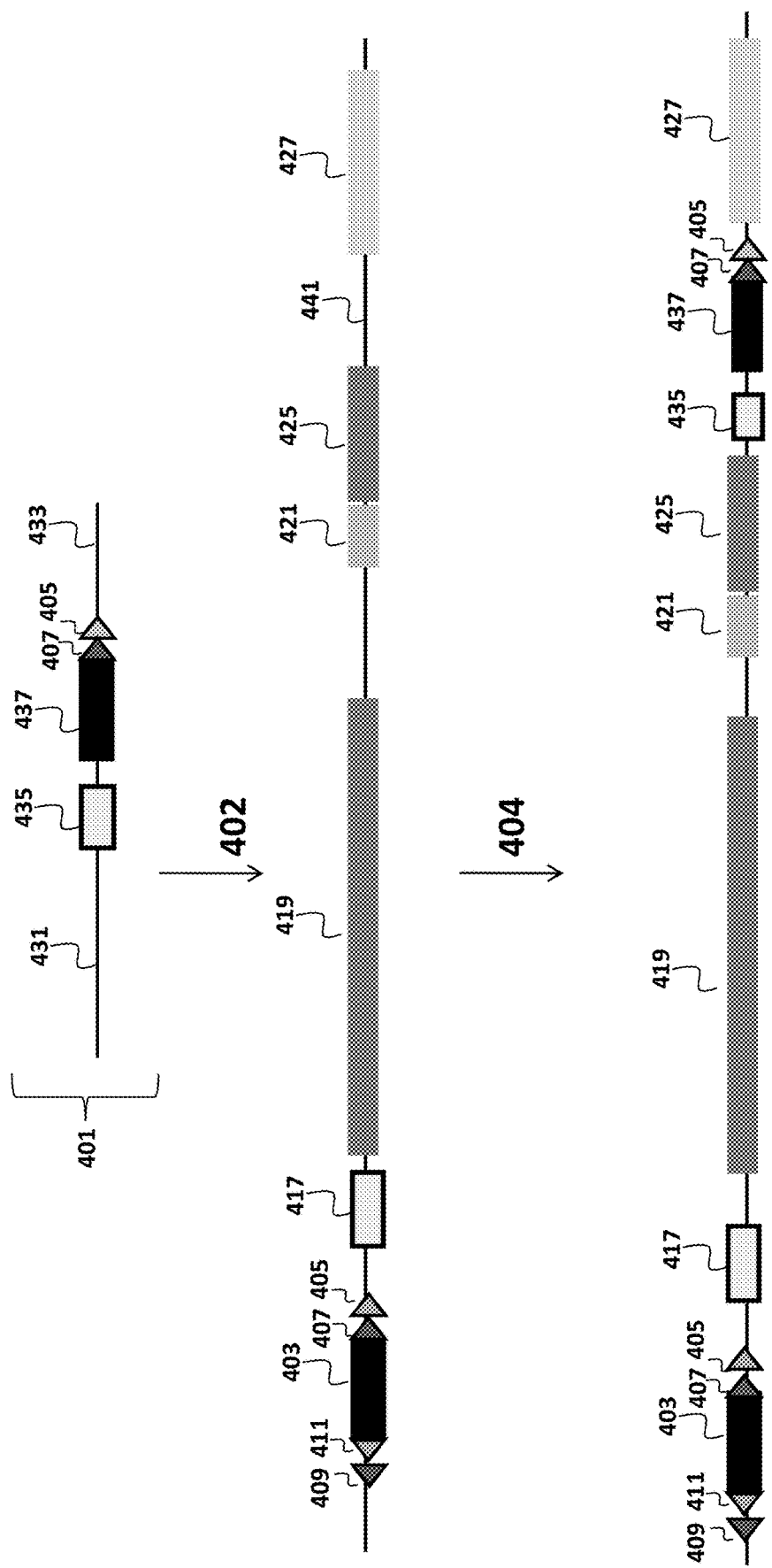
FIG. 4 is a schematic diagram illustrating the introduction of a second set of site-specific recombination sites into the genome of a non-human mammalian cell via a homology targeting vector.

As illustrated in FIG. 4, a second homology targeting vector 401 is provided comprising a hypoxanthinephosphoribosyltransferase (HPRT) mini-gene 435 and a neomycin resistance gene 437 and recombinase recognition sites FRT 407 and loxP 405, for Flp and Cre, which have the ability to recombine with FRT 407 and loxP 405 sites integrated from the first homology targeting vector. The regions 431 and 433 are homologous to the 5' and 3' portions, respectively, of a contiguous region 441 in the endogenous mouse locus that is 3' of the genomic region comprising the mouse endogenous $V_H$, D and J genes and 5' of the constant gene region. The homology targeting vector 401 is introduced 402 to the modified mouse immunoglobulin region, which comprises the endogenous $V_H$ genes 419, the pre-D region 421, the J gene region 425 and the constant gene region 427. The site specific recombination sites and the HPRT mini-gene 435 and a neomycin resistance gene 437 of the homology targeting vector 401 is integrated 404 into the mouse genome 5' of the mouse endogenous $V_H$ gene region.

Figure 5:
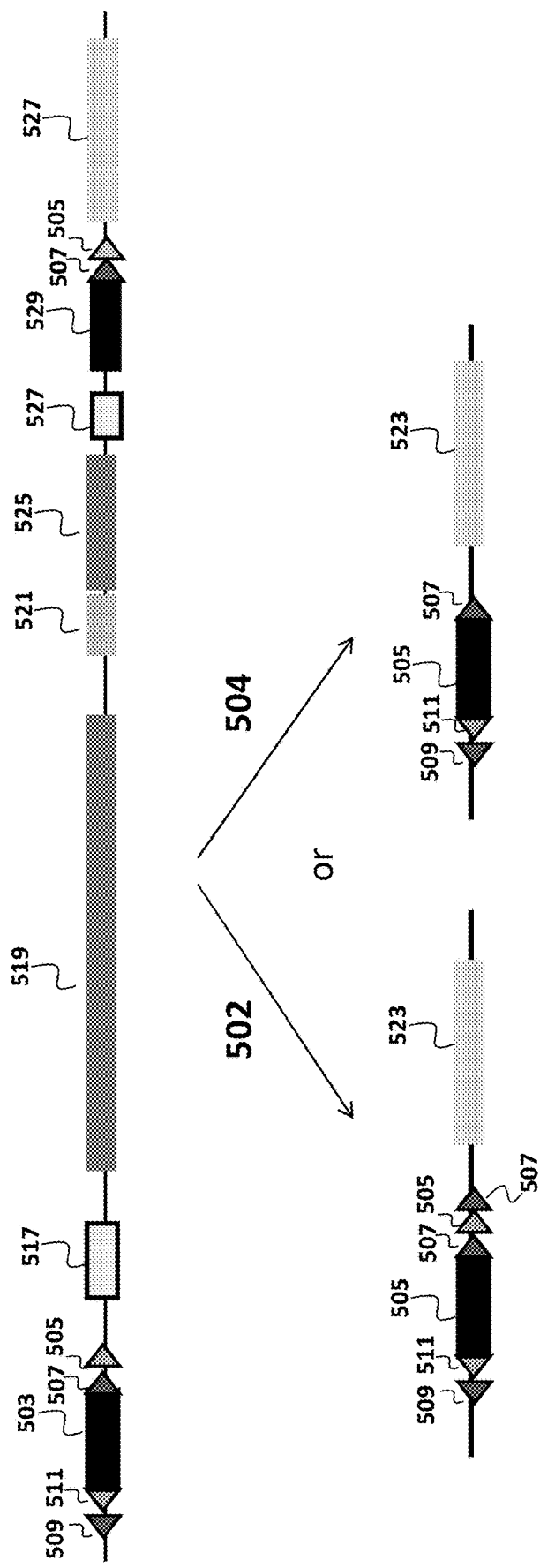
FIG. 5 is a schematic diagram illustrating deletion of the endogenous immunoglobulin region of the host cell.

Once the recombination sites are introduced to the host mammal's genome, the endogenous region of the immunoglobulin domain is then subject to recombination by introducing one of the recombinases corresponding to the site-specific recombination sites in the genome, in this example either FLP or Cre. As illustrated in FIG. 5, when FLP is introduced 502, the region containing the site-specific recombination sites (509, 511, 507 and 505) and the puroΔTK gene 503 are retained, with an additional FLP recombination site 507 now present 3' of the other two recombination sites 507 and 505. The region 3' of the recombination sites—including the hDTR 517, the endogenous immunoglobulin domain (519, 521, 525), and the HPRT 527 and Neo 529 genes introduced using the second homology targeting vector are deleted. When Cre is used for recombinase-mediated deletion 504, the area of deletion is the same, but only one site specific recombination site 507 remains directly 3' of the puroΔTK gene. The procedure depends on the second targeting having occurred on the same chromosome rather than on its homolog (i.e., in cis rather than in trans). If the targeting occurs in trans, the cells will not be sensitive to negative selection after Cre recombination.

The primary screening for deletion of the endogenous immunoglobulin region can be carried out by Southern blot, or with primary polymerase chain reaction (PCR) screens supported by secondary screens with Southern and/or loss-of-native-allele qPCR screens. HPRT will allow for (6-thioguanine-dependent) negative selection in HPRT-deficient ES cells. ES cells with a deleted immunoglobulin region can be selected by negative selection using the hDTR gene.

Figure 6:
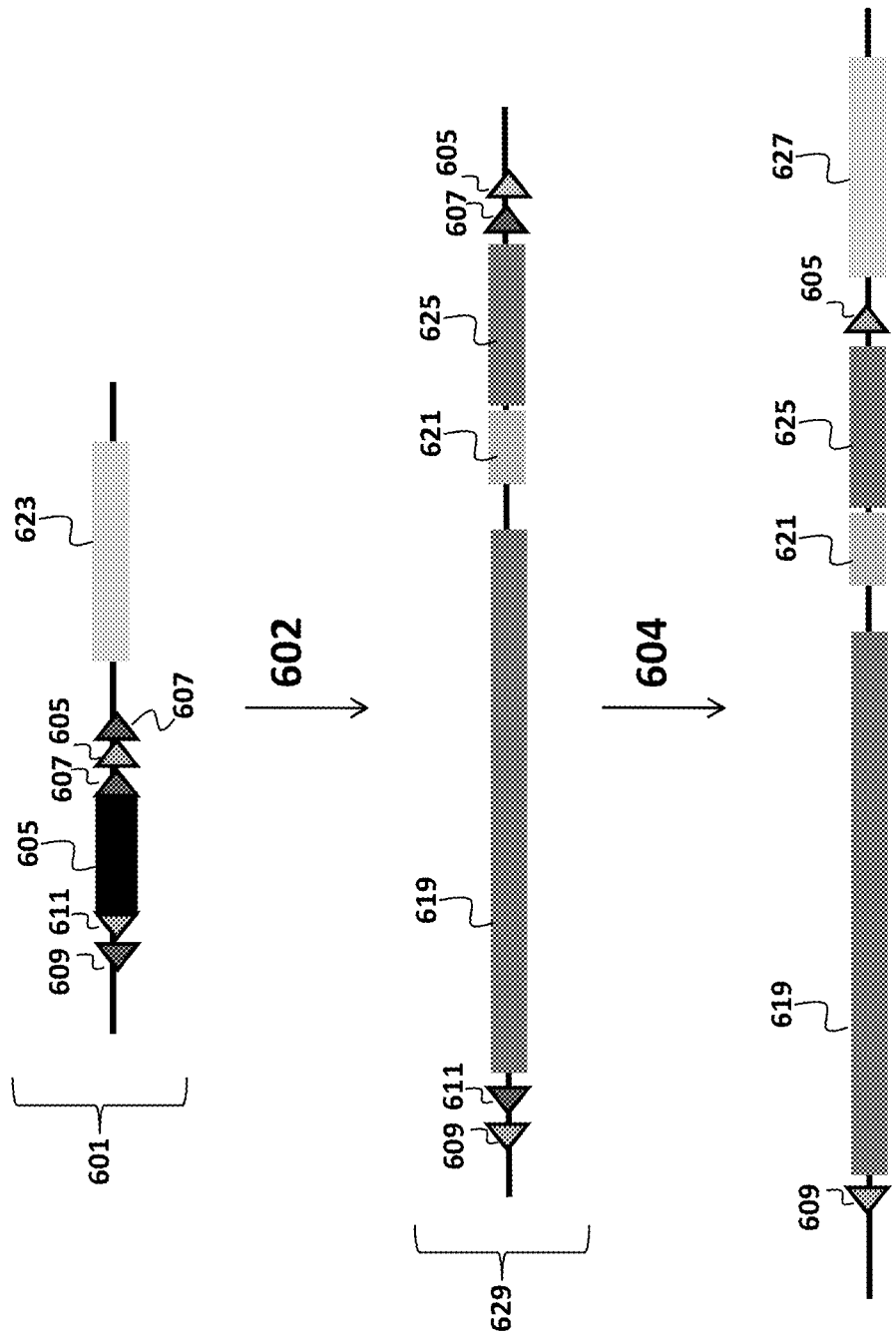
FIG. 6 is a schematic diagram illustrating the introduction of the partially human immunoglobulin region via a site specific targeting vector.

FIG. 6 illustrates the introduction of the partially human sequence to the modified mouse genome. A site-specific targeting vector 629 comprising the partially human immunoglobulin region 610 to be introduced to the mammalian host genome is introduced 602 to the genomic region 601 with the deleted endogenous immunoglobulin region comprising the site-specific recombination sites (609, 611, 607 and 605) and the puroΔTK gene 603. The site-specific targeting vector comprised a partially human immunoglobulin region comprising i) a $V_H$ region 619 comprising 44 human $V_H$ coding regions and intervening sequences based on the mouse genome endogenous sequences; ii) a 10 kb pre-DJ region 621 comprising mouse sequence; and iii) a DJ region 625 comprising human D and J gene coding regions and intervening sequences based on the mouse genome endogenous sequences. The partially human immunoglobulin region is flanked by recombination sites (609, 611, 605 and 607) that will allow recombination with the modified endogenous locus. Upon introduction of the appropriate recombinase 604, the partially human immunoglobulin region is integrated into the genome upstream of the constant gene region 627.

The primary screening for introduction of the partially human immunoglobulin region can be carried out by Southern blot, or with primary PCR screens supported by secondary screens with Southern and/or loss-of-native-allele qPCR screens. The deletion of the HPRT gene 605 as part of the recombination event will allow identification of the cells that did not undergo the recombination event using (6-thioguanine-dependent) negative selection.

Figure 7:
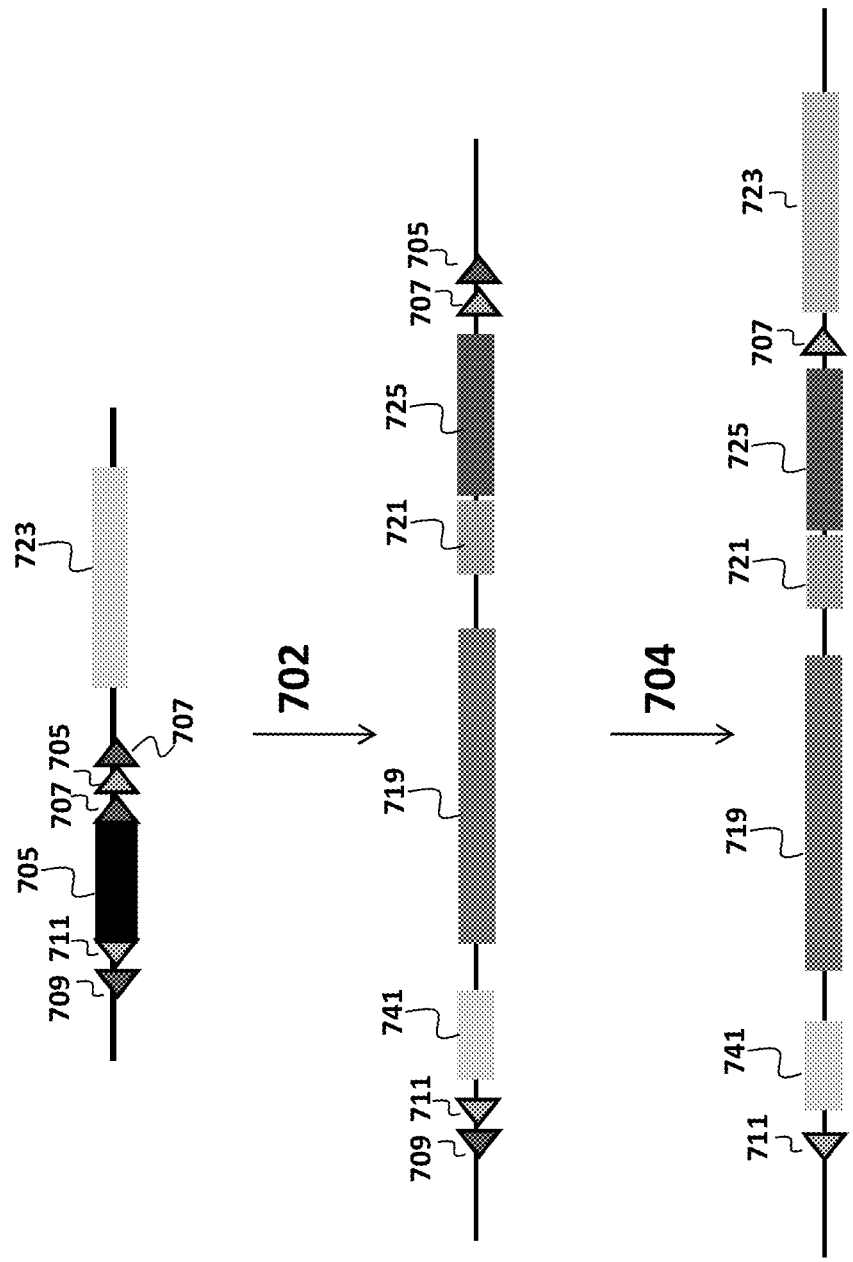
FIG. 7 is a schematic diagram illustrating the introduction of the partially human immunoglobulin region comprising additional mouse sequences using a site specific targeting vector.

Example 2: Introduction of a Partially Human Immunoglobulin Region into a Mouse Genome In certain aspects, the partially human immunoglobulin region will comprise the elements as described in Example 1, but with additional sequences e.g., sequences strategically added to introduce additional regulatory sequences, to ensure desired spacing within the introduced immunoglobulin region, to ensure that certain coding sequences are in adequate juxtaposition with other sequences adjacent to the replaced immunoglobulin region, and the like. FIG. 7 illustrates the introduction of a second exemplary partially human sequence to the modified mouse genome as produced in FIGS. 2-5 and described in Example 1 above.

A site-specific targeting vector 729 comprising the partially human immunoglobulin region 710 to be introduced to the mammalian host genome is introduced 702 to the genomic region 701 with the deleted endogenous immunoglobulin region comprising the site-specific recombination sites (709, 711, 707 and 705) and the puroΔTK gene 703. The site-specific targeting vector comprised a partially human immunoglobulin region comprising i) a $V_H$ region 719 comprising 1-43 human $V_H$ coding regions and intervening sequences based on the mouse genome endogenous sequences; ii) a 10 kb pre-DJ region 721 comprising mouse sequence; iii) a DJ region 725 comprising human D and J coding regions and intervening sequences based on the mouse genome endogenous sequences; and iv) a mouse non-functional $J_H$ gene region. The partially human immunoglobulin region is flanked by recombination sites 709, 711, 705 and 707) that will allow recombination with the modified endogenous locus. Upon introduction of the appropriate recombinase 704, the partially human immunoglobulin region is integrated into the genome upstream of the constant gene region 727.

As described in Example 1, the primary screening for introduction of the partially human immunoglobulin region can be carried out by Southern blot, or with primary PCR screens supported by secondary screens with Southern and/or loss-of-native-allele qPCR screens. The deletion of the HPRT gene 705 as part of the recombination event will allow identification of the cells that did not undergo the recombination event using (6-thioguanine-dependent) negative selection.

Figure 8:
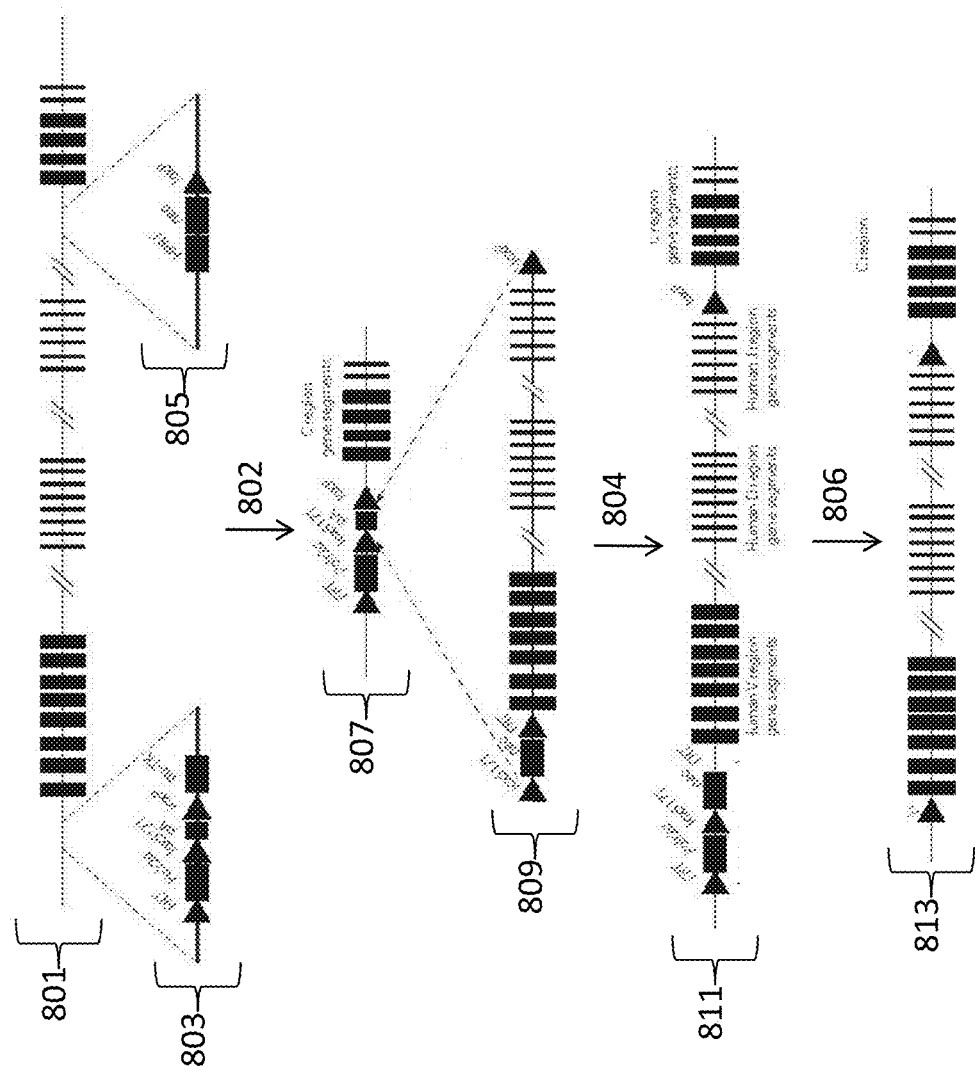
FIG. 8 is a schematic diagram illustrating the introduction of the partially human immunoglobulin region comprising additional mouse sequences to a mouse heavy chain region.

Example 3: Introduction of a Partially Human Immunoglobulin Region into the Immunoglobulin Heavy Chain Gene Locus of a Mouse Genome A method for replacing a portion of a mammalian genome with partially human immunoglobulin region is illustrated in FIG. 8. This method used introduction of a first site-specific recombination site into the mammalian genome followed by the introduction of a second site-specific recombination site into the mammalian genome. The two sites flanked the entire cluster of $V_H$, $D_H$ and $J_H$ region gene segments. The flanked endogenous region was deleted using the relevant site-specific recombinase, as described herein.

The targeting vectors 803, 805 employed for introducing the site-specific recombinase sites on either side of the $V_H$, $D_H$ and $J_H$ region gene segment cluster in the wild-type mouse immunoglobulin region 801 included an additional site-specific recombinase site that has been modified so that it is still recognized efficiently by the recombinase, but will not recombine with unmodified sites. This site was positioned in the targeting vector such that after deletion of the $V_H$, $D_H$ and $J_H$ region gene segment cluster it could be used for a second site specific recombination event in which a non-native piece of DNA is moved into the modified $V_H$ locus. The process of moving the DNA into the locus using the site-specific recombinase is referred to as "recombinase-mediated cassette exchange". In this example, the non-native DNA was a synthetic nucleic acid comprising both human and non-human sequences.

Two gene targeting vectors were constructed to accomplish the process just outlined. One of the vectors 803 comprised mouse genomic DNA taken from the 5' end of the locus, upstream of the most distal variable region gene segment. The other vector 805 comprised mouse genomic DNA taken from within the locus in the vicinity of the J region gene segments.

The key features of the 5' vector 803 in order from 5' to 3' were as follows: a gene encoding the diphtheria toxin A (DTA) subunit under transcriptional control of a modified herpes simplex virus type I thymidine kinase gene promoter coupled to two mutant transcriptional enhancers from the polyoma virus; 4.5 Kb of mouse genomic DNA mapping upstream of the most distal variable region gene segment in the heavy chain locus; a J region gene segment (disabled); an FRT recognition sequence for the Flp recombinase; a piece of genomic DNA containing the mouse Polr2a gene promoter; a translation initiation sequence (methionine codon embedded in a "Kozak" consensus sequence); a mutated loxP recognition sequence (known as a lox5171 site) for the Cre recombinase; a transcription termination/polyadenylation sequence; a loxP recognition sequence for the Cre recombinase; a gene encoding a fusion protein comprised of a protein conferring resistance to puromycin fused to a truncated form of the thymidine kinase (pu-TK) under transcriptional control of the promoter from the mouse phosphoglycerate kinase 1 gene; and 3 Kb of mouse genomic DNA mapping close to the 4.5 Kb sequence in the vector and arranged in the native relative orientation.

The key features of the 3' vector 805 in order from 5' to 3' were as follows: a gene encoding the diphtheria toxin A (DTA) subunit under transcriptional control of a modified herpes simplex virus type I thymidine kinase gene promoter coupled to two mutant transcriptional enhancers from the polyoma virus; 3.7 Kb of mouse genomic DNA containing the mouse J region gene segments oriented such that the end of the region that maps closest to the heavy chain variable region gene segments was closest to the DTA gene in the vector; a minigene encoding the human hypoxanthine-guanine phosphoribosyl transferase (HPRT) under transcriptional control of the mouse Polr2a gene promoter; a neomycin resistance gene under the control of the mouse phosphoglycerate kinase 1 gene promoter; a loxP recognition sequence for the Cre recombinase; and 2.1 Kb of mouse genomic DNA that maps immediately downstream in the genome of the 3.7 Kb fragment with the two fragments oriented in the same configuration as in the mouse genome.

Mouse embryonic stem (ES) cells (derived from C57B1/6NTac mice) were transfected by electroporation with the 3' vector 805 according to widely used procedures. Prior to electroporation, the vector DNA was linearized with the NotI restriction enzyme. The transfected cells were plated and after ≥24 hours they were placed under drug selection using the neomycin analogue G418. Colonies of drug-resistant ES cells were physically extracted from their plates after they became visible to the naked eye over a week later.

These picked colonies were disaggregated, re-plated in micro-well plates, and cultured for several days. Thereafter, each of the clones of cells was divided such that some of the cells could be frozen as an archive, and the rest used for isolation of DNA for analytical purposes.

DNA from the ES cell clones was screened by PCR using a widely used gene-targeting assay design. Four assays were used, and in each case one of the PCR oligonucleotide primer sequences mapped outside the region of identity shared between the 3' vector 805 and the genomic DNA, while the other mapped within the novel DNA between the two arms of genomic identity in the vector (i.e., in the HPRT or neo gene elements). According to the standard design, these assays were designed to detect pieces of DNA that would only be present in clones of cells derived from transfected cells that had undergone fully legitimate homologous recombination between the 3'heavy targeting vector and the genome.

Two separate transfections were performed with the 3' vector 805. The first of these yielded a total of two positive clones from approximately 300 clones screened using the four PCR assays. The second yielded a total of six positive clones, also from approximately 300 clones screened. A total of six PCR-positive clones from the two transfections were selected for expansion followed by further analysis using Southern blot assays.

The Southern blot assays are performed according to widely used procedures using three probes and genomic DNA digested with multiple restriction enzymes chosen so that the combination of probes and digests allow the structure of the targeted locus in the clones to be identified as properly modified by homologous recombination. One of the probes maps to DNA sequence flanking one side of the region of identity shared between the 3'heavy targeting vector and the genomic DNA; a second probe maps outside the region of identity but on its other side; and the third probe maps within the within the novel DNA between the two arms of genomic identity in the vector (i.e., in the HPRT or neo gene elements).

The six PCR-positive clones of ES cells are analyzed karyotypically using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the Southern blot data, and that also do not have detectable chromosomal aberrations based on the karyotype analysis, are selected for further use.

Acceptable clones are modified with the 5' vector 803 using procedures and screening assays that are essentially identical in design to those used with the 3' vector 805 except puromycin selection is used instead of G418/neomycin selection. The PCR assays, probes and digests are also tailored to match the genomic region being modified by the 5' vector 805.

Clones of ES cells that have been mutated in the expected fashion by both the 3'heavy and the 5'heavy vectors, i.e., doubly-targeted cells carrying both engineered mutations are isolated following vector targeting. The clones must have undergone gene targeting on the same chromosome, as opposed to homologous chromosomes (i.e., the engineered mutations created by the targeting vectors must be in cis on the same DNA strand rather than in trans on separate homologous DNA strands). Clones with the cis arrangement of mutations are distinguished from those with the trans arrangement by analytical procedures such as fluorescence in situ hybridization of metaphase spreads using probes that hybridize to the novel DNA present in the two gene targeting vectors between their arms of genomic identity. The two types of clones can also be distinguished from one another by transfecting them with a vector expressing the Cre recombinase and then comparing the number of colonies that survive gancyclovir selection against the thymidine kinase gene introduced by the 5' vector 803 and by analyzing the drug resistance phenotype of the surviving clones by a "sibling selection" screening procedure in which some of the cells from the clone are tested for resistance to puromycin or G418/neomycin. Cells with the cis arrangement of mutations are expected to yield approximately $10^3$ more gancyclovir-resistant clones than cells with the trans arrangement in this type of experiment. The majority of the resulting cis-derived gancyclovir-resistant clones are also be sensitive to both puromycin and G418/neomycin, in contrast to the trans-derived gancyclovir-resistant clones, which should retain resistance to both drugs. Doubly-targeted clones of cells with the cis-arrangement of engineered mutations in the heavy chain locus are selected for further use.

The doubly targeted clones of cells are transfected with a vector expressing the Cre recombinase and the transfected cells subsequently are placed under gancyclovir selection, as in the analytical experiment summarized above. Gancyclovir-resistant clones of cells are isolated and analyzed by PCR and Southern blot for the presence of the expected deletion between the two engineered mutations created by the 5'heavy and the 3'heavy targeting vectors. In these clones, the Cre recombinase causes a recombination 802 to occur between the loxP sites introduced into the heavy chain locus by the two vectors to create the construct shown at 807. Because the loxP sites are arranged in the same relative orientations in the two vectors, recombination results in excision of a circle of DNA comprising the entire genomic interval between the two loxP sites. The circle does not contain an origin of replication and thus will not be replicated during mitosis and will therefore be lost from the clones of cells as they undergo clonal expansion. The resulting clones carry a deletion of the DNA that was originally between the two loxP sites.

ES cell clones carrying the deletion of sequence in one of the two homologous copies of their immunoglobulin heavy chain locus are retransfected 804 with a Cre recombinase expression vector together with a piece of DNA 809 comprising a partially human immunoglobulin heavy chain locus containing V, D and J region gene segments. The key features of this piece of DNA 809 are the following: a lox5171 site; a neomycin resistance gene open reading frame (lacking the initiator methionine codon, but in-frame and contiguous with an uninterrupted open reading frame in the lox5171 site); a transcription termination/polyadenylation sequence; an FRT site; an array of 44 human heavy chain variable region gene segments, each comprised of human coding sequences embedded in mouse noncoding sequences; a 7.5 Kb piece of genomic DNA from immediately upstream of the cluster of D region gene segments in the mouse heavy chain locus; a 58 Kb piece of DNA containing the human D and J region gene segments; a loxP site in opposite relative orientation to the lox5171 site.

The transfected clones are placed under G418 selection, which enriches for clones of cells that have undergone a recombinase-mediated cassette exchange process in which the partially human donor DNA 809 (SEQ ID NO:1) is integrated in its entirety into the deleted immunoglobulin heavy chain locus between the loxP and lox5171 sites to create the DNA region illustrated at 811. The remaining elements from the 5' vector 803 are removed via FLP-mediated recombination 806 resulting in the final humanized locus as shown at 813.

G418-resistant ES cell clones are analyzed by PCR and Southern blot to determine if they have undergone the expected recombinase-mediated cassette exchange process without unwanted rearrangements or deletions. Clones that have the expected genomic structure are selected for further use.

ES cell clones carrying the partially human immunoglobulin heavy chain DNA 813 in the mouse heavy chain locus are microinjected into mouse blastocysts from strain DBA/2 to create partially ES cell-derived chimeric mice according to standard procedures. Male chimeric mice with the highest levels of ES cell-derived contribution to their coats will be selected for mating to female mice. The female mice of choice here will be of C57Bl/6NTac strain, and will also carry a transgene encoding the Flp recombinase that is expressed in their germline. Offspring from these matings are analyzed for the presence of the partially human immunoglobulin heavy chain locus, and for loss of the FRT-flanked neomycin resistance gene that was created in the recombinase-mediated cassette exchange step. Mice that carry the partially human locus will be used to establish a colony of mice.

Figure 9:
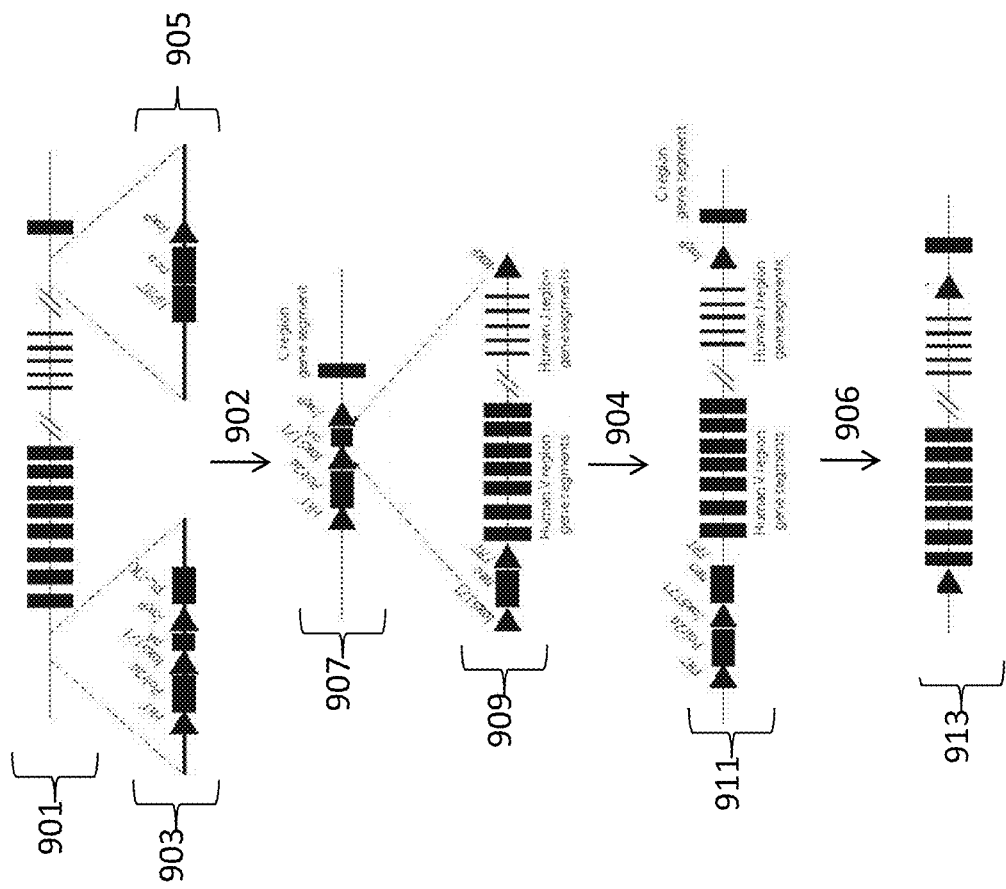
FIG. 9 is a schematic diagram illustrating the introduction of the partially human immunoglobulin region comprising additional mouse sequences to a mouse kappa region.

Example 4: Introduction of a Partially Human Immunoglobulin Region into the Immunoglobulin Kappa Chain Gene Locus of a Mouse Genome Another method for replacing a portion of a mammalian genome with partially human immunoglobulin region is illustrated in FIG. 9. This method provides introducing a first site-specific recombination site into the mammalian genome, which may be introduced either 5' or 3' of the main cluster of $V_K$ and $J_K$ region gene segments of the mammalian genome, followed by the introduction of a second site-specific recombination site into the mammalian genome, which in combination with the first site-specific recombination site flanks the entire cluster of $V_K$ and $J_K$ region gene segments. The flanked endogenous region can then be deleted and replaced using the relevant site-specific recombinase.

The targeting vectors employed for introducing the site-specific recombinase sites on either side of the $V_K$ and $J_K$ region gene segment cluster 901 also include an additional site-specific recombinase site that has been modified so that it is still recognized efficiently by the recombinase, but will not recombine with unmodified sites. This site is positioned in the targeting vector such that after deletion of the $V_K$ and $J_K$ region gene segment cluster it can be used for a second site specific recombination event in which a non-native piece of DNA is moved into the modified $V_K$ locus via recombinase-mediated cassette exchange. In this example, the non-native DNA is a synthetic nucleic acid comprising both human and non-human sequences.

Two gene targeting vectors were constructed to accomplish the process just outlined. One of the vectors 903 was comprised of mouse genomic DNA taken from the 5' end of the locus, upstream of the most distal variable region gene segment. The other vector 905 was comprised of mouse genomic DNA taken from within the locus in the vicinity of the J region gene segments.

The key features of the 5' vector 903 were as follows: a gene encoding the diphtheria toxin A (DTA) subunit under transcriptional control of a modified herpes simplex virus type I thymidine kinase gene promoter coupled to two mutant transcriptional enhancers from the polyoma virus; 6 Kb of mouse genomic DNA mapping upstream of the most distal variable region gene segment in the kappa chain locus; an FRT recognition sequence for the Flp recombinase; a piece of genomic DNA containing the mouse Polr2a gene promoter; a translation initiation sequence (methionine codon embedded in a "Kozak" consensus sequence); a mutated loxP recognition sequence (known as a lox5171 site) for the Cre recombinase; a transcription termination/polyadenylation sequence; a loxP recognition sequence for the Cre recombinase; a gene encoding a fusion protein comprised of a protein conferring resistance to puromycin fused to a truncated form of the thymidine kinase (pu-TK) under transcriptional control of the promoter from the mouse phosphoglycerate kinase 1 gene; 2.5 Kb of mouse genomic DNA mapping close to the 6 Kb sequence in the vector and arranged in the native relative orientation.

The key features of the 3' vector 905 were as follows: a gene encoding the diphtheria toxin A (DTA) subunit under transcriptional control of a modified herpes simplex virus type I thymidine kinase gene promoter coupled to two mutant transcriptional enhancers from the polyoma virus; 6 Kb of mouse genomic DNA taken from the vicinity of the kappa locus J region gene segments oriented such that end of the fragment that maps closest to the kappa variable region gene segments was closest to the DTA gene in the vector; a minigene encoding the human hypoxanthine-guanine phosphoribosyl transferase (HPRT) under transcriptional control of the mouse Polr2a gene promoter; a neomycin resistance gene under the control of the mouse phosphoglycerate kinase 1 gene promoter; a loxP recognition sequence for the Cre recombinase; 3.6 Kb of mouse genomic DNA that maps immediately downstream in the genome of the 6 Kb fragment also included in the vector, with the two fragments oriented in the same relative way as in the mouse genome.

Mouse embryonic stem (ES) cells derived from C57Bl/6NTac mice were transfected by electroporation with the 3' vector 905 according to widely used procedures. Prior to electroporation, the vector DNA was linearized with the NotI restriction enzyme. The transfected cells were plated and after ≥24 hours they were placed under drug selection using the neomycin analogue G418. Colonies of drug-resistant ES cells were physically extracted from their plates after they became visible to the naked eye over a week later. These picked colonies were disaggregated, re-plated in micro-well plates, and cultured for several days. Thereafter, each of the clones of cells was divided such that some of the cells could be frozen as an archive, and the rest used for isolation of DNA for analytical purposes.

DNA from the ES cell clones was screened by PCR using a widely used gene-targeting assay design. Four assays were used, and in each case one of the PCR oligonucleotide primer sequences mapped outside the region of identity shared between the 3' vector 905 and the genomic DNA 901, while the other mapped within the novel DNA between the two arms of genomic identity in the vector (i.e., in the HPRT or neo gene elements). According to the standard design, these assays were designed to detect pieces of DNA that would only be present in clones of cells derived from transfected cells that had undergone fully legitimate homologous recombination between the 3' vector 905 and the genome One transfection was performed with the 3' vector 905 and this yielded a total of seventeen positive clones from approximately 300 clones screened using the four PCR assays.

A total of six PCR-positive clones from the transfection were selected for expansion followed by further analysis using Southern blot assays. The Southern blot assays were performed according to widely used procedures; they involved three probes and genomic DNA digested with multiple restriction enzymes chosen so that the combination of probes and digests allowed for conclusions to be drawn about the structure of the targeted locus in the clones and whether it had been properly modified by homologous recombination. One of the probes mapped to DNA sequence flanking one side of the region of identity shared between the 3'kappa targeting vector and the genomic DNA; a second probe also mapped outside the region of identity but on its other side; and the third probe mapped within the within the novel DNA between the two arms of genomic identity in the vector (i.e., in the neo gene). The Southern blot identified the presence of the expected Eco911-generated fragment of DNA corresponding to the correctly mutated (by homologous recombination with the 3'kappa targeting vector) part of the kappa locus as detected by one of the external probes and by the neomycin probe (data not shown). The external probe detects the mutant fragment and also a wild-type fragment from the nonmutant copy of the immunoglobulin kappa locus on the homologous chromosome.

The six PCR-positive clones of ES cells were also analyzed karyotypically using an in situ fluorescence hybridization procedure designed to distinguish the most commonly arising chromosomal aberrations that arise in mouse ES cells. One clone with such an aberration was excluded from further use. Two karyoptypically normal clones that were judged to have the expected correct genomic structure based on the Southern blot data were selected for further use.

The two clones are modified with the 5' vector 903 using procedures and screening assays that are essentially identical in design to those used with the 3' vector 905, except puromycin selection is used instead of G418/neomycin selection, and the protocols are tailored to match the genomic region modified by the 5' vector 903. The goal of the 5' vector 903 transfection experiments is to isolate clones of ES cells that have been mutated in the expected fashion by both the 3' vector 905 and the 5' vector 903, i.e., doubly-targeted cells carrying both engineered mutations. In these clones, the Cre recombinase causes a recombination 902 to occur between the loxP sites introduced into the kappa locus by the two vectors to create the construct shown at 907.

Further, the clones must have undergone gene targeting on the same chromosome, as opposed to homologous chromosomes, i.e., the engineered mutations created by the targeting vectors must be in cis on the same DNA strand rather than in trans on separate homologous DNA strands. Clones with the cis arrangement of mutations are distinguished from those with the trans arrangement by analytical procedures such as fluorescence in situ hybridization of metaphase spreads using probes that hybridize to the novel DNA present in the two gene targeting vectors between their arms of genomic identity. The two types of clones can also be distinguished from one another by transfecting them with a vector expressing the Cre recombinase and comparing the number of colonies that survive gancyclovir selection against the thymidine kinase gene introduced by the 5' vector 903 and by analyzing the drug resistance phenotype of the surviving clones by a "sibling selection" screening procedure in which some of the cells from the clone are tested for resistance to puromycin or G418/neomycin.

Cells with the cis arrangement of mutations are expected to yield approximately $10^3$ more gancyclovir-resistant clones than cells with the trans arrangement in this type of experiment. The majority of the resulting cis-derived gancyclovir-resistant clones should also be sensitive to both puromycin and G418/neomycin, in contrast to the trans-derived gancyclovir-resistant clones, which should retain resistance to both drugs. Clones of cells with the cis-arrangement of engineered mutations in the kappa chain locus are selected for further use.

The doubly targeted clones of cells are transfected with a vector expressing the Cre recombinase and the transfected cells will subsequently be placed under gancyclovir selection, as in the analytical experiment summarized above. Gancyclovir-resistant clones of cells are isolated and analyzed by PCR and Southern blot for the presence of the expected deletion between the two engineered mutations created by the 5' vector 903 and the 3' vector 905. In these clones, the Cre recombinase has caused a recombination to occur between the loxP sites introduced into the kappa chain locus by the two vectors. Because the loxP sites are arranged in the same relative orientations in the two vectors, recombination results in excision of a circle of DNA comprising the entire genomic interval between the two loxP sites. The circle will not contain an origin of replication and thus will not be replicated during mitosis and will therefore be lost from the clones of cells as they undergo clonal expansion. The resulting clones carry a deletion of the DNA that was originally between the two loxP sites. Clones that have the expected deletion will be selected for further use.

The ES cell clones carrying the deletion of sequence in one of the two homologous copies of their immunoglobulin kappa chain locus, will be retransfected 904 with a Cre recombinase expression vector together with a piece of DNA 909 comprising a partially human immunoglobulin kappa chain locus containing V and J region gene segments. The key features of this piece of DNA (referred to as "K-K") (SEQ ID NO:2) are the following: a lox5171 site; a neomycin resistance gene open reading frame (lacking the initiator methionine codon, but in-frame and contiguous with an uninterrupted open reading frame in the lox5171 site); a transcription termination/polyadenylation sequence; an FRT site; an array of 39 human kappa variable region gene segments, each comprised of human coding sequences embedded in mouse noncoding sequences; a 13.5 Kb piece of genomic DNA from immediately upstream of the cluster of J kappa region gene segments in the mouse kappa chain locus; a 2 Kb piece of DNA containing 5 human J region gene segments embedded in mouse noncoding DNA; a loxP site in opposite relative orientation to the lox5171 site.

In a second independent experiment, an alternative piece of partially human DNA 909 is used in place of the K-K DNA. The key features of this DNA (referred to as "L-K") (SEQ ID NO:3) are the following: a lox5171 site; a neomycin resistance gene open reading frame lacking the initiator methionine codon, but in-frame and contiguous with an uninterrupted open reading frame in the lox5171 site; a transcription termination/polyadenylation sequence; an FRT site; an array of 38 human lambda variable region gene segments, each comprised of human coding sequences embedded in mouse noncoding sequences; a 13.5 Kb piece of genomic DNA from immediately upstream of the cluster of J region gene segments in the mouse kappa chain locus; a 2 Kb piece of DNA containing 5 human J lambda region gene segments embedded in mouse noncoding DNA; a loxP site in opposite relative orientation to the lox5171 site.

The transfected clones from the K-K (SEQ ID NO:2) and L-K (SEQ ID NO:3) transfection experiments are placed under G418 selection, which enriches for clones of cells that have undergone a recombinase-mediated cassette exchange process in which the partially human donor DNA is integrated in its entirety into the deleted immunoglobulin kappa chain locus between the loxP and lox5171 sites that were placed there by the 3' vectors 905 and 5' vectors 903 respectively. The DNA region created using the K-K sequence is illustrated at 911 in FIG. 9. The remaining elements from the 5' vector 903 are removed via FLP-mediated recombination 906 resulting in the final humanized locus as shown at 913.

G418-resistant ES cell clones are analyzed by PCR and Southern blot to determine if they have undergone the expected recombinase-mediated cassette exchange process without unwanted rearrangements or deletions. Both K-K and L-K clones that have the expected genomic structure are selected for further use.

The K-K ES cell clones and the L-K ES cell clones, each carrying the partially human immunoglobulin DNA in the mouse kappa chain locus, are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice for use in the mating are of the C57Bl/6NTac strain, and will also carry a transgene encoding the Flp recombinase that is expressed in their germline. Offspring from these matings are analyzed for the presence of the partially human immunoglobulin kappa chain locus, and for loss of the FRT-flanked neomycin resistance gene that was created in the recombinase-mediated cassette exchange step. Mice that carry the partially human locus are used to establish colonies of K-K and L-K mice.

Mice carrying the partially human (i.e., humanized) heavy chain locus, produced as described in Example 3, can be bred with mice carrying a humanized kappa chain locus. Their offspring are in turn bred together in a scheme that ultimately produces mice that are homozygous for both humanized loci, i.e., humanized for heavy chain and kappa. Such mice produce partially human heavy chains comprised of human variable domains and mouse constant domains. They also produce partially human kappa proteins comprised of human kappa variable domains and the mouse kappa constant domain from their kappa loci. Monoclonal antibodies recovered from these mice are comprised of human variable domains paired with human kappa variable domains.

A variation on the breeding scheme involves generating mice that are homozygous for the humanized heavy chain locus, but heterozygous at the kappa locus such that on one chromosome they have the K-K humanized locus and on the other chromosome they have the L-K humanized locus. Such mice produce partially human heavy chains comprised of human variable domains and mouse constant domains. They also produce partially human kappa proteins comprised of human kappa variable domains and the mouse kappa constant domain from one of their kappa loci. From the other kappa locus, they will produce partially human lambda proteins comprised of human lambda variable domains the mouse kappa constant domain. Monoclonal antibodies recovered from these mice are comprised of human variable domains paired in some cases with human kappa variable domains and in other cases with human lambda variable domains.

Figure 10:
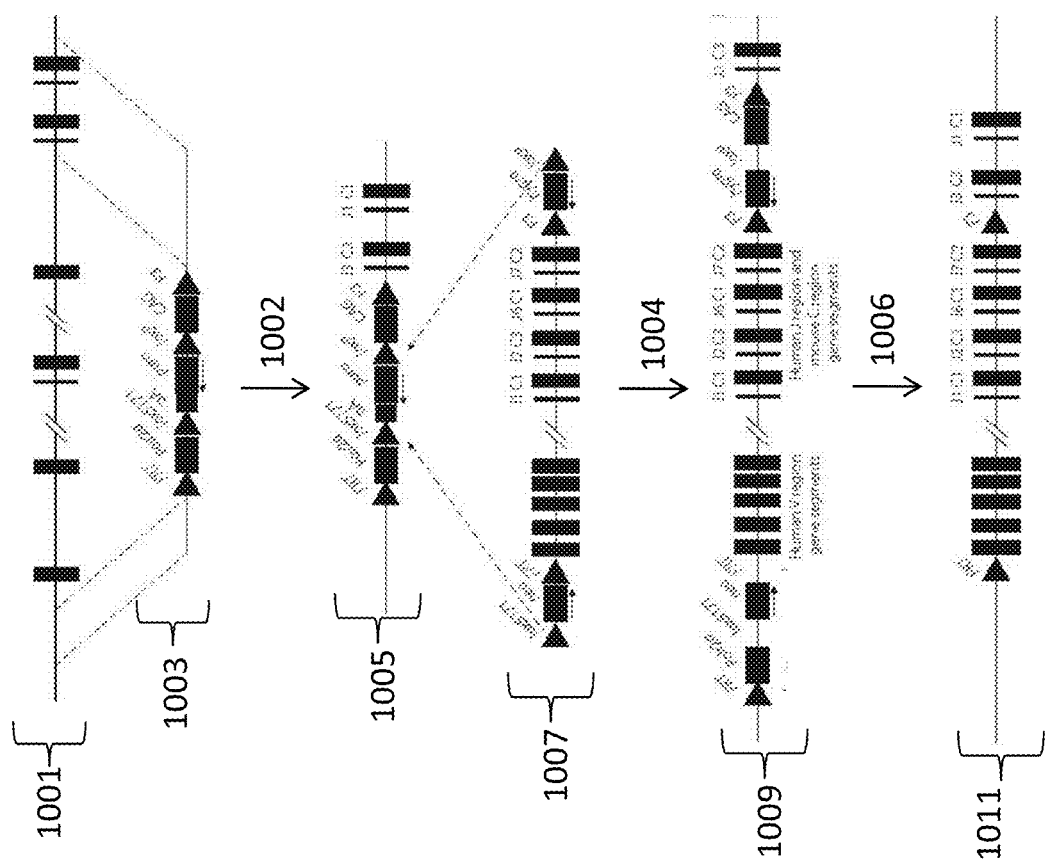
FIG. 10 is a schematic diagram illustrating the introduction of the partially human immunoglobulin region comprising additional mouse sequences to a mouse lambda region.

Example 5: Introduction of a Partially Human Immunoglobulin Region into the Immunoglobulin Lambda Chain Gene Locus of a Mouse Genome A method for replacing a portion of a mammalian genome with partially human immunoglobulin region is illustrated in FIG. 10. This method provides deleting approximately 194 Kb of DNA from the wild-type mouse immunoglobulin lambda locus 1001 by a homologous recombination process involving a targeting vector 1003 that shares identity with the locus both upstream of the V2 gene segment and downstream of the V1 gene segment in the immediate vicinity of the J3, C3, J1 and C1 gene segments. The vector replaces the 194 Kb of DNA with elements designed to permit a subsequent site-specific recombination in which a non-native piece of DNA is moved into the modified $V_L$ locus via recombinase-mediated cassette exchange 1002. In this example, the non-native DNA is a synthetic nucleic acid comprising both human and non-human sequences.

The key features of the gene targeting vector 1003 for accomplishing the 194 Kb deletion are as follows: a negative selection gene such as a gene encoding the A subunit of the diphtheria toxin or a herpes simplex virus thymidine kinase gene; 4 Kb of genomic DNA from 5' of the mouse V2 variable region gene segment in the lambda locus; an FRT site; a piece of genomic DNA containing the mouse Polr2a gene promoter; a translation initiation sequence (methionine codon embedded in a "Kozak" consensus sequence); a mutated loxP recognition sequence (known as a lox5171 site) for the Cre recombinase; a transcription termination/polyadenylation sequence; an open reading frame encoding a protein that confers resistance to puromycin; this open reading frame would be on the antisense strand relative to the Polr2a promoter and the translation initiation sequence next to it; it would also be followed by its own transcription termination/polyadenylation sequence; a loxP recognition sequence for the Cre recombinase; a translation initiation sequence (a methionine codon embedded in a "Kozak" consensus sequence) on the same, antisense strand as the puromycin resistance gene open reading frame; a chicken beta actin promoter and cytomegalovirus early enhancer element oriented such that it directs transcription of the puromycin resistance open reading frame, with translation initiating at the initiation codon downstream of the loxP site and continuing back through the loxP site into the puromycin open reading frame all on the antisense strand relative to the Polr2a promoter and the translation initiation sequence next to it; a mutated recognition site for the Flp recombinase known as an "F3" site; a 7.3 Kb of genomic DNA containing the J3, C3, J1 and C1 gene segments and surrounding sequences; a second negative selection gene such as a gene encoding the A subunit of the diphtheria toxin or a herpes simplex virus thymidine kinase gene.

Mouse embryonic stem (ES) cells (derived from C57Bl/6NTac mice) are transfected 1002 by electroporation with the targeting vector 1003 according to widely used procedures. The resulting construct 1005 will replace the native DNA with the sequences from the targeting vector 1003 in the 196 Kb region.

Prior to electroporation, the vector DNA is linearized with a rare-cutting restriction enzyme that cuts only in the prokaryotic plasmid sequence or the polylinker associated with it. The transfected cells are plated and after ≥24 hours placed under drug selection using puromycin. Colonies of drug-resistant ES cells are physically extracted from their plates after they became visible to the naked eye over a week later. These picked colonies are disaggregated, re-plated in micro-well plates, and cultured for several days. Thereafter, each of the clones of cells are divided such that some of the cells are frozen as an archive, and the rest used for isolation of DNA for analytical purposes.

DNA from the ES cell clones is screened by PCR using a widely used gene-targeting assay design. Four assays are used, and in each case one of the PCR oligonucleotide primer sequences maps outside the region of identity shared between the targeting vector and the genomic DNA, while the other maps within the novel DNA between the two arms of genomic identity in the vector (e.g., in the puro gene). According to the standard design, these assays detect pieces of DNA that would only be present in clones of cells derived from transfected cells that had undergone fully legitimate homologous recombination between the targeting vector 1003 and the native DNA 1001.

Approximately six PCR-positive clones from the transfection 1002 are selected for expansion followed by further analysis using Southern blot assays. The Southern blots involve three probes and genomic DNA from the clones that has been digested with multiple restriction enzymes chosen so that the combination of probes and digests allow identification of whether the DNA has been properly modified by homologous recombination.

The six PCR-positive clones of ES cells are analyzed karyotypically using an in situ fluorescence hybridization procedure designed to distinguish the most commonly arising chromosomal aberrations that arise in mouse ES cells. Clones that show evidence of aberrations will be excluded from further use. Karyoptypically normal clones that are judged to have the expected correct genomic structure based on the Southern blot data are selected for further use.

The ES cell clones carrying the deletion in one of the two homologous copies of their immunoglobulin lambda chain locus are retransfected 1004 with a Cre recombinase expression vector together with a piece of DNA 1007 (SEQ ID NO:4) comprising a partially human immunoglobulin lambda chain locus containing V, J and C region gene segments. The key features of this piece of DNA 1007 are as follows: a lox5171 site; a neomycin resistance gene open reading frame (lacking the initiator methionine codon, but in-frame and contiguous with an uninterrupted open reading frame in the lox5171 site); a transcription termination/polyadenylation sequence; an FRT site; an array of 38 human lambda variable region gene segments, each comprised of human lambda coding sequences embedded in mouse lambda noncoding sequences; an array of J-C units where each unit is comprised of a human J lambda region gene segment and a mouse lambda constant domain gene segment embedded within noncoding sequences from the mouse lambda locus (the human J region gene segments will be those encoding J1, J2, J6 and J7, while the mouse lambda constant domain gene segments will be C1 and/or C2 and/or C3); a mutated recognition site for the Flp recombinase known as an "F3" site; an open reading frame conferring hygromycin resistance; the open reading frame is located on the antisense strand relative to the immunoglobulin gene segment coding information in the construct; a loxP site in opposite relative orientation to the lox5171 site.

The transfected clones are placed under G418 and/or hygromycin selection, which enriches for clones of cells that have undergone a recombinase-mediated cassette exchange process in which the partially human donor DNA is integrated in its entirety into the deleted immunoglobulin lambda chain locus between the loxP and lox5171 sites that were placed there by the gene targeting vector. The remaining elements from the targeting vector 1003 are removed via FLP-mediated recombination 1006 resulting in the final humanized locus as shown at 1011.

G418/hygromycin-resistant ES cell clones are analyzed by PCR and Southern blot to determine if they have undergone the expected recombinase-mediated cassette exchange process without unwanted rearrangements or deletions. Clones that have the expected genomic structure will be selected for further use.

The ES cell clones carrying the partially human immunoglobulin DNA 1011 in the mouse lambda chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here will be of C57B1/6NTac strain, which carry a transgene encoding the Flp recombinase expressed in their germline. Offspring from these matings are analyzed for the presence of the partially human immunoglobulin lambda chain locus, and for loss of the FRT-flanked neomycin resistance gene and the F3-flanked hygromycin resistance gene that were created in the recombinase-mediated cassette exchange step. Mice that carry the partially human locus are used to establish a colony of mice.

In some aspects, the mice comprising the humanized heavy chain and kappa locus (as described in Examples 3 and 4) are bred to mice that carry the humanized lambda locus. Mice generated from this type of breeding scheme are homozygous for the humanized heavy chain locus, and can be homozygous for the K-K humanized locus or the L-K humanized locus. Alternatively, they can be heterozygous at the kappa locus carrying the K-K locus on one chromosome and the L-K locus on the other chromosome. Each of these mice will be homozygous for the humanized lambda locus. Monoclonal antibodies recovered from these mice will be comprised of human variable domains paired in some cases with human kappa variable domains and in other cases with human lambda variable domains. The lambda variable domains will derive from either the humanized L-K locus or the humanized lambda locus.

Figure 11:
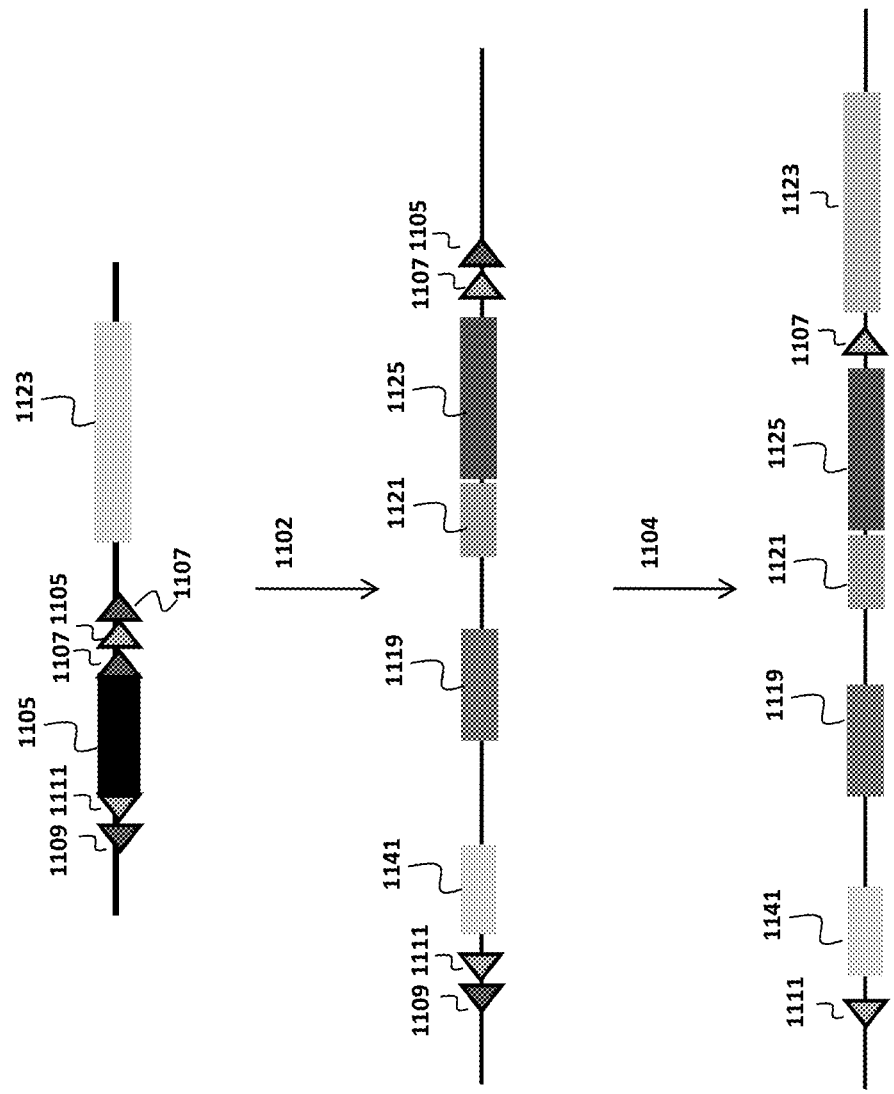
FIG. 11 is a schematic diagram illustrating the introduction of the partially human immunoglobulin region comprising a human $V_H$ minigene via a site specific targeting vector.

Example 6: Introduction of a Partially Human Immunoglobulin Minigene into a Mouse Genome In certain other aspects, the partially human immunoglobulin region will comprise a human variable domain minigene such as the one illustrated in FIG. 11. Here instead of a partially human immunoglobulin region comprising all or substantially all of the human $V_H$ genes, the mouse immunoglobulin region is replaced with a minigene 1119 comprising fewer human $V_H$ genes, e.g. 1-43 human $V_H$ genes.

A site-specific targeting vector 1129 comprising the partially human immunoglobulin region 1110 to be introduced to the mammalian host genome is introduced 1102 to the genomic region 1101 with the deleted endogenous immunoglobulin region comprising the site-specific recombination sites (1109, 1111, 1107 and 1105) and the puroΔTK gene 1103. The site-specific targeting vector comprised a partially human immunoglobulin region comprising i) a $V_H$ region 1119 comprising all 44 human $V_H$ coding regions and intervening sequences based on the mouse genome endogenous sequences; ii) a 10 kb pre-DJ region 721 comprising mouse sequence; iii) a DJ region 1125 comprising human D and J coding regions and intervening sequences based on the mouse genome endogenous sequences; and iv) a mouse non-functional $J_H$ gene region. The partially human immunoglobulin region is flanked by recombination sites 1109, 1111, 1105 and 1107) that will allow recombination with the modified endogenous locus. Upon introduction of the appropriate recombinase 1104, the partially human immunoglobulin region is integrated into the genome upstream of the constant gene region 1127.

As described in Example 1, the primary screening for introduction of the partially human immunoglobulin variable region locus can be carried out by Southern blot, or with primary PCR screens supported by secondary screens with Southern and/or loss-of-native-allele qPCR screens. The deletion of the HPRT gene 1105 as part of the recombination event will allow identification of the cells that did not undergo the recombination event using (6-thioguanine-dependent) negative selection.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

What is claimed is:

1. A method of producing an antibody for therapeutic or diagnostic use, the method comprising:
   (i) contacting a transgenic mouse whose genome comprises an endogenous mouse immunoglobulin locus variable region which has been deleted and replaced with an engineered immunoglobulin locus variable region comprising at least one of each of a chimeric V, D and J immunoglobulin variable region gene segment at the immunoglobulin heavy chain locus, and/or at least one of each of a chimeric V and J variable gene segment at the immunoglobulin light chain loci, wherein each chimeric gene segment comprises human V, D or J immunoglobulin variable region coding sequences embedded in mouse immunoglobulin variable region non-coding gene segment sequences with an antigen,
   (ii) expressing an antibody with a human variable domain cloned from an antibody-producing cell of the transgenic mouse of (i); and
   (iii) isolating the antibody with the human variable domain from the cell of (ii), wherein the antibody is for therapeutic or diagnostic use.

2. The method of claim 1, wherein the antibody is cloned from a B-cell of the transgenic mouse.

3. A method of producing a therapeutic or diagnostic antibody with human variable domains, the method comprising:
   (i) cloning a human variable domain of an antibody expressed by an antibody-producing cell from a transgenic mouse whose genome comprises an endogenous mouse immunoglobulin locus variable region which has been deleted and replaced with an engineered immunoglobulin locus variable region comprising at least one of each of a chimeric V, D and J immunoglobulin variable region gene segment at the immunoglobulin heavy chain locus, and/or at least one of each of a chimeric V and J variable gene segment at the immunoglobulin light chain loci, wherein each chimeric gene segment comprises human V, D or J immunoglobulin variable region coding sequences embedded in mouse immunoglobulin variable region non-coding gene segment sequences; and
   (ii) producing the therapeutic or diagnostic antibody comprising the human variable domain of the antibody expressed by the transgenic mouse; wherein said transgenic mouse has been contacted with an antigen.

4. The method of claim 3, wherein the human variable domain is cloned from an antibody expressed by a B-cell from the transgenic mouse.

5. A method of producing a monoclonal antibody comprising a human variable domain, the method comprising:
   (i) providing B-cells from a transgenic mouse whose genome comprises an endogenous mouse immunoglobulin locus variable region which has been deleted and replaced with an engineered immunoglobulin locus variable region comprising at least one of each of a chimeric V, D and J immunoglobulin variable region gene segment at the immunoglobulin heavy chain locus, and/or at least one of each of a chimeric V and J variable gene segment at the immunoglobulin light chain loci, wherein each chimeric gene segment comprises human V, D or J immunoglobulin variable region coding sequences embedded in mouse immunoglobulin variable region non-coding gene segment sequences;
   (ii) immortalizing the B-cells; and
   (iii) isolating monoclonal antibodies comprising human variable domains expressed by the immortalized B-cells, or genes encoding the antibodies wherein said transgenic mouse has been contacted with an antigen.

6. The method of claim 5, further comprising:
   (iv) cloning the human variable domains expressed by the B-cells; and
   (v) producing a therapeutic or diagnostic antibody comprising the human variable domain cloned from the B-cells of the transgenic mouse.

7. A method of producing antibodies comprising human variable domains, the method comprising contacting a transgenic mouse whose genome comprises an endogenous mouse immunoglobulin locus variable region which has been deleted and replaced with an engineered immunoglobulin locus variable region comprising at least one of each of a chimeric V, D and J immunoglobulin variable region gene segment at the immunoglobulin heavy chain locus, and/or at least one of each of a chimeric V and J variable gene segment at the immunoglobulin light chain loci with an antigen, wherein each chimeric gene segment comprises human V, D or J immunoglobulin variable region coding sequences embedded in mouse immunoglobulin variable region non-coding gene segment sequences, wherein the engineered immunoglobulin locus of the transgenic mouse expresses antibodies comprising human variable domains.

8. The method of claim 7, further comprising isolating the antibodies comprising human variable regions expressed by the transgenic mouse, or genes encoding the antibodies.

9. The method of claim 7, further comprising:
   (i) obtaining B-cells from the transgenic mouse expressing antibodies specific for the antigen;
   (ii) immortalizing the B-cells; and
   (iii) isolating antibodies specific for the target antigen from the immortalized B-cells.

10. The method of claim 9, further comprising cloning human variable regions from the B-cells specific for the particular antigen.

11. The method of claim 10, further comprising producing a therapeutic or diagnostic antibody using the human variable regions cloned from the B-cells.

* * * * *